US008501400B2

(12) United States Patent
Mulvey et al.

(10) Patent No.: US 8,501,400 B2
(45) Date of Patent: *Aug. 6, 2013

(54) METHODS AND COMPOSITIONS FOR DETERMINING THE PATHOGENIC STATUS OF INFECTIOUS AGENTS

(75) Inventors: Matthew C. Mulvey, Baltimore, MD (US); Leo Einck, McLean, VA (US); Katherine Sacksteder, Baltimore, MD (US)

(73) Assignee: Sequella, Inc., Rockville, MD (US)

( * ) Notice: Subject to any disclaimer, the term of this patent is extended or adjusted under 35 U.S.C. 154(b) by 155 days.

This patent is subject to a terminal disclaimer.

(21) Appl. No.: 13/011,754

(22) Filed: Jan. 21, 2011

(65) Prior Publication Data

US 2011/0212457 A1 Sep. 1, 2011

Related U.S. Application Data

(63) Continuation-in-part of application No. 12/080,929, filed on Apr. 7, 2008, now Pat. No. 7,919,234.

(60) Provisional application No. 60/922,213, filed on Apr. 5, 2007, provisional application No. 60/927,217, filed on May 2, 2007, provisional application No. 61/297,056, filed on Jan. 21, 2010, provisional application No. 61/371,646, filed on Aug. 6, 2010.

(51) Int. Cl.
*C12Q 1/02* (2006.01)
*C12Q 1/68* (2006.01)
*C12Q 1/70* (2006.01)
*C07H 21/02* (2006.01)
*C12N 15/00* (2006.01)

(52) U.S. Cl.
USPC ............... 435/5; 435/6.1; 435/29; 435/320.1

(58) Field of Classification Search
None
See application file for complete search history.

(56) References Cited

U.S. PATENT DOCUMENTS

| 5,478,727 | A | 12/1995 | Roizman et al. |
| 5,773,267 | A | 6/1998 | Jacobs et al. |
| 5,994,137 | A | 11/1999 | Jacobs et al. |
| 6,300,061 | B1 | 10/2001 | Jacobs, Jr. et al. |
| 6,833,135 | B1 | 12/2004 | Frazao Moniz Pereira |
| 2002/0156016 | A1 | 10/2002 | Minuk |
| 2009/0047658 | A1 | 2/2009 | Mulvey et al. |
| 2009/0155768 | A1 | 6/2009 | Scholl et al. |
| 2010/0330678 | A1* | 12/2010 | Soucaille .................. 435/471 |

FOREIGN PATENT DOCUMENTS

| WO | WO 93/16172 A1 | 8/1993 |
| WO | WO 94/25572 A1 | 11/1994 |
| WO | WO 97/22713 A1 | 6/1997 |
| WO | WO 99/16868 A1 | 4/1999 |
| WO | WO 2006/075996 A2 | 7/2006 |
| WO | WO 2008/131230 A1 | 10/2008 |

OTHER PUBLICATIONS

Archie, Nina—PCT Officer, PCT IPRP, International Preliminary Report on Patentability Appl. No. PCT/US08/04491, pp. 1-7, Mar. 26, 2012.
EPO Exam Report issued in Appl. No. 08742606.0, *EPO Exam Report*, pp. 1-10, Mar. 22, 2012.
International Search Report issued in PCT/US08/04491, *PCT—International Search Report*, pp. 1-8, Jun. 20, 2008.
Albert et al., Performance of a Rapid Phage-Based Test, *FASTPlaqueTB™*, to Diagnose Pulmonary Tuberculosis from Sputum Specimens in South Africa, *International Journal of Tuberculosis and Lung Disease*, vol./Iss. 6(6), pp. 529-537, Jun. 1, 2002.
Albert et al., Simple, Phage-Based *FASTPlaque*TB™ Technology to Determine Rifampicin Resistance of *Mycobacterium tuberculosis* Directly from Sputum, *International Journal of Tuberculosis and Lung Disease*, vol./Iss. 8(9), pp. 1114-1119, Sep. 1, 2004.
Cavusoglu et al., Evaluation of the Genotype MTBDR Assay for Rapid Detection of Rifampin and Isoniazid Resistance in *Mycobacterium tuberculosis* Isolates, *Journal of Clinical Microbiology*, vol./Iss. 44(7), pp. 2338-2342, Jul. 1, 2006.
Dye et al., Consensus Statement. Global Burden of Tuberculosis: Estimated Incidence, Prevalence, and Mortality by County. WHO Global Surveillance and Monitoring Project (Abstract only—Applicants do not have complete copy), *Journal of the American Medical Association*, vol./Iss. 282(7), pp. 677-686, Aug. 18, 1999.
EPO Extended Search Report—Appl. No. 08742606.0, *EPO Extended Search Report*, pp. 1-11, Jul. 13, 2011.
Lwoff, A., The Concept of Virus, *The Journal of General Microbiology*, vol./Iss. 17(1), pp. 239-253, Aug. 28, 1957.
Miotto et al., Use of Genotype MTBDR Assay for Molecular Detection of Rifampin and Isoniazid Resistance in *Mycobacterium tuberculosis* Clinical Strains Isolated in Italy, *Journal of Clincial Microbiology*, vol./Iss. 44(7), pp. 2485-2491, Jul. 1, 2006.
Notice of Allowance and Examiner's Amendment cited in U.S. Appl. No. 12/080,929, *USPTO Notice of Allowance*, pp. 1-9, Mar. 3, 2011.
Office Action issued in U.S. Appl. No. 12/080,929, *USPTO Office Action*, pp. 1-9, Jul. 8, 2010.
Neufeld et al., Electrochemical Phagemid Assay for the Specific Detection of Bacteria using *Escherichia coli* TG-1 and the M13K07 Phagemid in a Model System (XP 002393930), *Analytical Chemistry, American Chemical Society*, vol./Iss. 77(2), pp. 652-657, Dec. 16, 2004.

(Continued)

*Primary Examiner* — Albert Navarro
(74) *Attorney, Agent, or Firm* — F. Brent Nix; Johnson, Marcou & Isaacs, LLC

(57) ABSTRACT

The present invention relates to methods and compositions for improved detection of infectious agents and microbes. In particular, the present invention provides novel methods for detecting infectious agents, providing information about the viability status of such infectious agents and for determining drug susceptibility. In certain embodiments, the present invention employs techniques involving nucleic acid amplification-based microbial identification together with phage-based biological detection of drug resistance. The methods of the invention are suitable for all microbes and infectious agents, including bacterial agents such as *Mycobacteria*.

40 Claims, 26 Drawing Sheets

OTHER PUBLICATIONS

International Search Report and Written Opinion dated Nov. 16, 2012 for PCT/US2011/022161.

Stanley et al., "Development of a New, Combined Rapid Method Using Phage and PCT for Detection and Identification of Viable *Mycobacterium* Paratuberculosis Bacteria within 48 hours," Applied and Environment Microbiology, Jan. 26, 2007, vol. 73, pp. 1851-1857.

Serganov et al., "Ribozymes, Riboswitches and Beyond: Regulation of Gene Expression without Proteins," Nature Reviews Genetics, Sep. 11, 2007, vol. 8, pp. 776-790.

Hornig, H., EPO Office Action issued in European Application No. 08742606.0, pp. 1-9, Jan. 24, 2013.

* cited by examiner

Diagnosis: Species B is pathogen. Prescribe Drug 2

A.

B.

SEQUENCE LISTING

<160> NUMBER OF SEQ ID NOS: 3

<210> SEQ ID NO 1
<211> LENGTH: 939
<212> TYPE: DNA
<213> ORGANISM: Artificial Sequence
<220> FEATURE:
<223> OTHER INFORMATION: Synthetic

<400> SEQUENCE: 1

```
gcggccgcaa gcagcataac cttttccgt gatggtaact tcacggtaac caagatgtcg      60
agttaaccac ccaaggccat ccgtcaggat ggccttgttt aaacctctgc acaggcacgt     120
ctggatgcac gtcgccgcgc aggtatggct cgcggtcttt aattgcctat ttaggtgaca     180
ctatagaagt taattaattg gttctacata aatgcctaac gactatccct ttggggagta     240
gggtcaagtg actcgaaacg atagacaact tgctttaaca agttggagat atagtctgct     300
ctgcatggtg acatgcagct ggatataatt ccggggtaag attaacgacc ttatctgaac     360
ataatgctac cgtttaatat tcgtggcctt tgtcaccgac gcctactcga gggggttaatg    420
taaaaaccga ccagaatcat gcaagtgcgt aagatagtcg cgggccggga aaaacattgg     480
cccctcgagg gacaacgccg aattgcgaag ggctatcagt ttaatgtgcg taaacgacca     540
catcaaccat gcatgatctt ctactacatc agcttttaga ttttcacgc ttactgcttt       600
tttcttccca agatcgaaaa tttactgaat taacaatgga ttctgaggtt gctgctttgg     660
ttattgataa cggttctggt atgtgtaaag ccggagctca gatgtttcct tgggttaatt     720
gaggcctgag tataaggtga cttatacttg taatctatct aaacggggaa cctctctagt     780
agacaatccc gtgctaaatt gtaggactgc cctccggacc tatgccctat ctaccttgcg     840
taggtagggt tcttttagc ataacccctt ggggcctcta aacgggtctt gaggggtttt      900
tttatcctta atccttagcg aaagctaagg attttttt                              939
```

<210> SEQ ID NO 2
<211> LENGTH: 24
<212> TYPE: DNA
<213> ORGANISM: Artificial Sequence
<220> FEATURE:
<223> OTHER INFORMATION: Synthetic

<400> SEQUENCE: 2

```
taggcgtcgg tgacaaaggc cacg                                              24
```

<210> SEQ ID NO 3
<211> LENGTH: 24
<212> TYPE: DNA
<213> ORGANISM: Artificial Sequence
<220> FEATURE:

<223> OTHER INFORMATION: Synthetic

<400> SEQUENCE: 3
ggacaacgcc gaattgcgaa gggc                                        24

METHODS AND COMPOSITIONS FOR DETERMINING THE PATHOGENIC STATUS OF INFECTIOUS AGENTS

CROSS REFERENCE TO RELATED APPLICATIONS

This application is a continuation-in-part of U.S. patent application Ser. No. 12/080,929, filed Apr. 7, 2008 now U.S. Pat. No. 7,919,234, allowed, which claims the benefit of U.S. Provisional Patent Application No. 60/922,213, filed Apr. 5, 2007, U.S. Provisional Patent Application No. 60/927,217, filed May 2, 2007. This application further claims the benefit of U.S. Provisional Patent Application No. 61/297,056 filed Jan. 21, 2010, and U.S. Provisional Patent Application No. 61/371,646 filed Aug. 6, 2010.

FIELD OF THE INVENTION

The present invention relates to methods and compositions for improved detection of infectious agents and microbes. In particular, the present invention provides novel methods for detecting infectious agents, providing information about the viability status of such infectious agents and for determining drug susceptibility. In certain embodiments, the present invention employs techniques involving nucleic acid amplification-based microbial identification together with phage-based biological detection of drug resistance. The methods of the invention are suitable for all microbes and infectious agents, including bacterial agents such as *Mycobacteria*.

BACKGROUND OF THE INVENTION

When penicillin became widely available during the second world war, it was a medical miracle, rapidly vanquishing the biggest wartime killer-infected wounds. Discovered initially by a French medical student, Ernest Duchesne, in 1896, and then rediscovered by Scottish physician Alexander Fleming in 1928, the product of the soil hold Penicillium crippled many types of disease-causing bacteria. But just four years after drug companies began mass-producing penicillin in 1943, microbes began appearing that could resist it.

The first bug to battle penicillin was *Staphylococcus aureus*. This bacterium is often a harmless passenger in the human body, but it can cause illness, such as pneumonia or toxic shock syndrome, when it overgrows or produces a toxin. In 1967, another type of penicillin-resistant pneumonia, caused by *Streptococcus pneumoniae* and called pneumococcus, surfaced in a remote village in Papua New Guinea. At about the same time, American military personnel in Southeast Asia were acquiring penicillin-resistant gonorrhea from prostitutes. By 1976, when the soldiers had come home, they brought the new strain of gonorrhea with them, and physicians had to find new drugs to treat it. In 1983, a hospital-acquired intestinal infection caused by the bacterium *Enterococcus faecium* joined the list of bugs that outwit penicillin. Antibiotic resistance spreads fast. Between 1979 and 1987, for example, only 0.02 percent of pneumococcus strains infecting a large number of patients surveyed by the National Centers for Disease Control and Prevention (CDC) were penicillin-resistant. The CDC's survey included 13 hospitals in 12 states. By 1994, 6.6 percent of pneumococcus strains were resistant, according to a report in the Jun. 15, 1994, Journal of the American Medical Association by Robert F. Breiman, M.D., and colleagues at CDC. The agency also reports that in 1992, 13,300 hospital patients died of bacterial infections that were resistant to antibiotic treatment. (R. Lewis "The Rise of Antibiotic Resistant Infections" www.fda.gov). According to experts in the field such as Michael Blum, M.D. (medical officer in the Food and Drug Administration's division of anti-infective drug products), one of the main contributors of the alarming increase in antibiotic-resistant infections was a result of complacency: "There was complacency in the 1980s. The perception was that we had licked the bacterial infection problem. Drug companies weren't working on new agents. They were concentrating on other areas, such as viral infections. In the meantime, resistance increased to a number of commonly used antibiotics, possibly related to overuse of antibiotics. In the 1990s, we've come to a point for certain infections that we don't have agents available." According to a report in the Apr. 28, 1994, New England Journal of Medicine, researchers have identified bacteria in patient samples that resist all currently available antibiotic drugs.

The increased prevalence of antibiotic resistance is an outcome of evolution. Any population of organisms, bacteria included, naturally includes variants with unusual traits, in this case the ability to withstand an antibiotic's attack on a microbe. When a person takes an antibiotic, the drug kills the defenseless bacteria, leaving behind—or "selecting," in biological terms—those that can resist it. These renegade bacteria then multiply, increasing their numbers a million-fold in a day, becoming the predominant microorganism.

The antibiotic does not technically cause the resistance, but allows it to happen by creating a situation where an already existing variant can flourish. "Whenever antibiotics are used, there is selective pressure for resistance to occur. It builds upon itself. More and more organisms develop resistance to more and more drugs," says Joe Cranston, Ph.D., Director of the Department of Drug Policy and Standards at the American Medical Association in Chicago. A patient can develop a drug-resistant infection either by contracting a resistant bug to begin with, or by having a resistant microbe emerge in the body once antibiotic treatment begins. Drug-resistant infections increase risk of death, and are often associated with prolonged hospital stays, and sometimes complications. These might necessitate removing part of a ravaged lung, or replacing a damaged heart valve.

Disease-causing microbes thwart antibiotics by interfering with their mechanism of action. For example, penicillin kills bacteria by attaching to their cell walls, then destroying a key part of the wall. The wall falls apart, and the bacterium dies. Resistant microbes, however, either alter their cell walls so penicillin can't bind or produce enzymes that dismantle the antibiotic. In another scenario, erythromycin attacks ribosomes, structures within a cell that enable it to make proteins. Resistant bacteria have slightly altered ribosomes to which the drug cannot bind. The ribosomal route is also how bacteria become resistant to the antibiotics tetracycline, streptomycin and gentamicin.

Mycobacterial Disease

Mycobacterial infections often manifest as diseases such as tuberculosis. Human infections caused by *Mycobacteria* have been widespread since ancient times, and tuberculosis remains a leading cause of death today. Although the incidence of the disease declined, in parallel with advancing standards of living, since the mid-nineteenth century, mycobacterial diseases still constitute a leading cause of morbidity and mortality in countries with limited medical resources. Additionally, mycobacterial diseases can cause overwhelming, disseminated disease in immunocompromised patients. In spite of the efforts of numerous health organizations worldwide, the eradication of mycobacterial diseases has never been achieved, nor is eradication imminent.

Nearly one third of the world's population is infected with *Mycobacterium tuberculosis* complex, commonly referred to as tuberculosis, with approximately 8 million new cases, and two to three million deaths attributable to tuberculosis yearly. Tuberculosis is the cause of the largest number of human deaths attributable to a single etiologic agent (1). After decades of decline, tuberculosis is now on the rise. In the United States, up to 10 million individuals are believed to be infected. Almost 28,000 new cases were reported in 1990, constituting a 9.4 percent increase over 1989. A sixteen percent increase in tuberculosis cases was observed from 1985 to 1990. Overcrowded living conditions and shared air spaces are especially conducive to the spread of tuberculosis, contributing to the increase in instances that have been observed among prison inmates, and among the homeless in larger U.S. cities.

Approximately half of all patients with "Acquired Immune Deficiency Syndrome" (AIDS) will acquire a mycobacterial infection, with tuberculosis being an especially devastating complication. AIDS patients are at higher risks of developing clinical tuberculosis, and anti-tuberculosis treatment seems to be less effective than in non-AIDS patients. Consequently, the infection often progresses to a fatal disseminated disease. *Mycobacteria* other than *M. tuberculosis* are increasingly found in opportunistic infections that plague the AIDS patient. Organisms from the *M. avium-intraceliulare* complex (MAC), especially serotypes four and eight, account for 68% of the mycobacterial isolates from AIDS patients. Enormous numbers of MAC are found (up to $10^{10}$ acid-fast bacilli per gram of tissue), and consequently, the prognosis for the infected AIDS patient is poor.

The World Health Organization (WHO) continues to encourage the battle against tuberculosis, recommending prevention initiatives such as the "Expanded Program on Immunization" (EPI), and therapeutic compliance initiatives such as "Directly Observed Treatment Short-Course" (DOTS). For the eradication of tuberculosis, diagnosis, treatment, and prevention are equally important. Rapid detection of active tuberculosis patients will lead to early treatment by which about 90% cure is expected. Therefore, early diagnosis is critical for the battle against tuberculosis. In addition, therapeutic compliance will ensure not only elimination of infection, but also reduction in the emergence of drug-resistance strains.

Although over 37 species of *Mycobacterium* have been identified, more than 95% of all human infections are caused by six species of *mycobacteria: M. tuberculosis, M. avium intracellulare, M. kansasii, M. fortueitum, M. chelonae*, and *M. leprae*. Cases of human tuberculosis are predominantly caused by mycobacterial species comprising *M. tuberculosis, M. bovis*, or *M. africanum* (2). Infection is typically initiated by the inhalation of infectious particles, which are able to reach the terminal pathways in the lungs. Following engulfment by alveolar macrophages, the bacilli are able to replicate freely, with eventual destruction of the phagocytic cells. A cascade effect ensues wherein destruction of the phagocytic cells causes additional macrophages and lymphocytes to migrate to the site of infection, where they too are ultimately eliminated. The disease is further disseminated during the initial stages by the infected macrophages, which travel to local lymph nodes, as well as into the blood stream and other tissues such as the bone marrow, spleen, kidneys, bone and central nervous system. (See Murray et al. Medical Microbiology. The C.V. Mosby Company 219-30 (1990).

There is still no clear understanding of the factors that contribute to the virulence of *mycobacteria*. Many investigators have implicated lipids of the cell wall and bacterial surface as contributors to colony morphology and virulence. Evidence suggests that C-mycosides, glycopeptidolipids on the surface of certain mycobacterial cells, are important in facilitating survival of the organism within macrophages. Trehalose 6,6' dimycolate, a cord factor, has been implicated for other *mycobacteria*.

The interrelationship of colony morphology and virulence is particularly pronounced in *M. avium*. *M. avium* bacilli occur in several distinct colony forms. Bacilli which grow as transparent, or rough, colonies on conventional laboratory media are multiplicable within macrophages in tissue culture, are virulent when injected into susceptible mice, and are resistant to antibiotics. Rough or transparent bacilli, which are maintained on laboratory culture media, often spontaneously assume an opaque colony morphology, at which time they are not multiplicable in macrophages, are avirulent in mice, and are highly susceptible to antibiotics. The differences in colony morphology between the transparent, rough and opaque strains of *M. avium* are almost certainly due to the presence of a glycolipid coating on the surface of transparent and rough organisms, which acts as a protective capsule. This capsule, or coating, is composed primarily of C-mycosides, which apparently shield the virulent *M. avium* organisms from lysosomal enzymes and antibiotics. By contrast, the non-virulent opaque forms of *M. avium* have very little C-mycoside on their surface. Both the resistance to antibiotics and the resistance to killing by macrophages have been attributed to the glycolipid barrier on the surface of *M. avium*.

The emergence of drug-resistant *M. tuberculosis* is an extremely disturbing phenomenon. The rate of new tuberculosis cases proven resistant to at least one standard drug increased from 10 percent in the early 1980's to 23 percent in 1991. Compliance with therapeutic regimens, therefore, is also a crucial component in efforts to eliminate tuberculosis and prevent the emergence of drug resistant strains. Equally important in the development of new therapeutic agents that are effective as vaccines, and as treatments, for disease caused by drug resistant strains of *mycobacteria*.

Multidrug-resistant tuberculosis (MDR-TB) is a form of tuberculosis that is resistant to two or more of the primary drugs used for the treatment of tuberculosis. Resistance to one of several forms of treatment occurs when bacteria develop the ability to withstand antibiotic attack and relay that ability to their progeny. Since an entire strain of bacteria inherit this capacity to resist the effects of various treatments, resistance can spread from one person to another.

The World Health Organization (WHO) estimates that up to 50 million persons worldwide may be infected with drug resistant strains of tuberculosis. Also, 300,000 new cases of MDR-TB are diagnosed around the world each year and 79 percent of the MDR-TB cases now show resistance to three or more drugs routinely used to treat tuberculosis. According to WHO, nearly 1 billion people will be infected with tuberculosis within the next decade if more effective preventative procedures are not adopted.

In 2003, the CDC reported that 7.7 percent of tuberculosis cases in the U.S. were resistant to INH, a first line drug used to treat tuberculosis. The CDC also reported that 1.3 percent of tuberculosis cases in the U.S. were resistant to both INH and RIF. RIF is the drug most commonly used with INH.

Clearly, the possibility of drug resistant strains of tuberculosis that develop during or before treatment are a major concern to health organizations and health care practitioners. Drugs used in the treatment of tuberculosis include, but are not limited to, ethambutol (EMB), pyrazinamide (PZA), streptomycin (STR), isoniazid (INH), moxifloxacin (MOX), and rifampicin (RIF). The exact course and duration of treatment can be tailored to a specific individual, however several strategies are well known to those skilled in the art.

The standard treatment for tuberculosis caused by drug-sensitive organisms is a six-month regimen consisting of four drugs given for two months, followed by two drugs given for four months. The two most important drugs, given throughout the six-month course of therapy, are INH and RIF. Although the regimen is relatively simple, its administration is quite complicated. Daily ingestion of eight or nine pills is often required during the first phase of therapy; a daunting and confusing prospect. Even severely ill patients are often symptom free within a few weeks, and nearly all appear to be cured within a few months. If the treatment is not continued to completion, however, the patient may experience a relapse, and the relapse rate for patients who do not continue treatment to completion is high. A variety of forms of patient-centered care are used to promote adherence with therapy. The most effective way of ensuring that patients are taking their medication is to use directly observed therapy, which involves having a member of the health care team observe the patient take each dose of each drug. Directly observed therapy can be provided in the clinic, the patient's residence, or any mutually agreed upon site. Nearly all patients who have tuberculosis caused by drug-sensitive organisms, and who complete therapy will be cured, and the risk of relapse is very low (3).

The FDA approved a medication that combines the three main drugs (INH, RIF, and PZA) used to treat tuberculosis into one pill. This reduces the number of pills a patient has to take each day and makes it impossible for the patient to take only one of the three medications, a common path to the development of MDR-TB. Despite this, there is still a need in the art to treat tuberculosis, especially in those cases wherein the tuberculosis strain is drug resistant.

Key to stemming the spread of drug-resistant tuberculosis is the development of rapid and accurate diagnostics to identify MDR-TB and extreme drug resistant tuberculosis (XDR-TB) infection. Gold-standard antibiotic susceptibility tests (AST) require several weeks or months to perform because they measure the growth of this notoriously slow-growing bacteria. Regardless of the time required for conducting AST, these techniques remain important and valuable as they are very accurate because they biologically measure the effect an antimicrobial has on a tuberculosis isolate.

Traditional diagnosis of mycobacterial infection is confirmed by the isolation and identification of the pathogen, although conventional diagnosis is based on sputum smears, chest X-ray examination (CXR), and clinical symptoms. Isolation of *mycobacteria* on an agar culture plate takes as long as four to eight weeks. Species identification takes a further two weeks. There are several other techniques for detecting *mycobacteria* such as the polymerase chain reaction (PCR), *mycobacterium tuberculosis* direct test, or amplified *mycobacterium tuberculosis* direct test (MID), and detection assays that utilize radioactive labels. Most of these tests are often cumbersome, require a high level of technical expertise and require long periods of time before useful results can be obtained.

One diagnostic test that is widely used for detecting infections caused by *M. tuberculosis* is the tuberculin skin test. Although numerous versions of the skin test are available, typically one of two preparations of tuberculin antigens are used: old tuberculin (OT), or purified protein derivative (PPD). The antigen preparation is either injected into the skin intradermally, or is topically applied and is then invasively transported into the skin with the use of a multiprong inoculator (Tine test). Several problems exist with the skin test diagnosis method. For example, the Tine test is not generally recommended because the amount of antigen injected into the intradermal layer cannot be accurately controlled (4).

Although the tuberculin skin tests are widely used, they typically require two to three days to generate results, and many times, the results are inaccurate since false positives are sometimes seen in subjects who have been exposed to *mycobacteria*, but are healthy. In addition, instances of misdiagnosis are frequent since a positive result is observed not only in active tuberculosis patients, but also in persons vaccinated with Bacille Calmette-Guerin (BCG), and those who had been infected with *mycobacteria*, but have not developed the disease. It is hard, therefore, to distinguish active tuberculosis patients from the others, such as household tuberculosis contacts, by the tuberculin skin test. Additionally, the tuberculin test often produces a cross-reaction in those individuals who were infected with *mycobacteria* other than *M. tuberculosis* (MOTT). Therefore, diagnosis using the skin tests currently available is frequently subject to error and inaccuracies.

Traditional methods to identify drug resistant strains of *M. tuberculosis* (Mtb) involve culturing Mtb isolated from clinical specimens in either liquid culture or on solid supports such as LJ slants or agar plates supplemented with the appropriate nutrient media for growth of *mycobacteria*. After the culture reaches a sufficient population density allowing visual identification of bacterial growth either by an increase in turbidity of a liquid culture or by colony formation on LJ slants or agar plates, the isolate is sub-cultured into two or more individual vessels either containing a different antibiotic or none at all. The effect of the antibiotic on the Mtb isolate is determined by comparing the growth of the antibiotic-containing subculture to one in which no drug was added. If the Mtb isolate is susceptible to the antibiotic, it will not grow sufficiently compared to the control. However, if the strain is resistant to the anti-tuberculosis drug, then it will continue to grow as it has the ability to circumvent the antimicrobial properties of the antibiotic. Second-generation versions of this biological, growth-based assay speed the time to detection of both microbial identification as well as resistance testing by using radiometric (e.g. Becton Dickinson's BACTEC™) or colorimetric (e.g. Becton Dickinson's MGIT™ and Biomerieux's BACT ALERT®) devices to measure or $CO_2$ produced by growing Mtb, rather than waiting for the bacterial population to reach a density sufficient to be seen by the naked eye.

More recent approaches to speed the biological detection of drug resistance in Mtb have focused on lysing mycobacteriophage to probe the effect an anti-microbial has on an Mtb isolate. Mycobacteriophage are viruses that infect *Mycobacteria* and hijack cellular biosynthetic machines to replicate and spread. Broadly speaking, viruses are obligate intracellular parasites: they rely on the biosynthetic machinery of the host cell to manufacture progeny in order to reproduce and spread. The extent to which an infecting virus is able to direct the synthesis and production of new viral components is largely dictated by the metabolic capacity (i.e. the viability status) of the host cell. In the extreme version, a living cell, which is metabolically active, can be infected by a virus and be co-opted for the production of new virus while a dead, metabolically inactive cell, cannot. Therefore, the extent to which a virus is able to infect and replicate in a host cell indicates the metabolic capacity of that cell. Because antibiotics ultimately affect the metabolic capacity of a susceptible bacterial cell, and phage hijack the biosynthetic machines of the host, antibiotics also have an effect on the replication and spread of bacteriophage. Furthermore, phage are able to find and infect small numbers of bacteria and because they replicate and spread so much faster than the host cell, especially in the case of Mtb, they can be used to dramatically speed the detection and antibiotic susceptibility test (AST) of Mtb.

Biotec, Inc.'s (Suffolk, United Kingdom) product FASTPLAQUE-RESPONSE™ measures the ability of the mycobacteriophage D29 to replicate inside Mtb after exposure to antibiotics. Mtb isolated from a clinical specimen are split into two vessels: one contains the anti-microbial rifampicin (RIF) while the other contains no antibiotic and serves as a positive control. After RIF is given sufficient time to exert its effects on Mtb, D29 is added to both tubes and given sufficient time to inject its DNA into Mtb and hijack the cell to make progeny virus. Prior to lysis of Mtb by phage-encoded lysis functions, extracellular phage that did not infect Mtb are killed by addition of a chemical virucide, which cannot penetrate inside Mtb and therefore kills all extra-cellular phage. The virucide and antibiotic are then removed and a fast-growing *mycobacteria, M. smegmatis* (Msmeg), is added to the phage-infected Mtb. The mixture is then plated onto agar dishes. Because Msmeg replicates quickly, a bacterial lawn is formed on the agar plates after overnight incubation at 37° C. Furthermore, Msmeg is efficiently infected by D29, which forms clear and visible plaques on Msmeg bacterial lawns. Each plaque represents an Mtb cell that was initially infected by D29 and produced progeny phage. This assay quantitatively measures D29 replication in small numbers of Mtb. Furthermore, because phage replication is wholly dependent upon the metabolic capacity of the host cell, quantitative measurements of D29 replication in Mtb exposed to an anti-microbial compared to an untreated control accurately measures the extent to which that antibiotic can disrupt Mtb metabolism, and ultimately bacterial growth. Low viral replication reflects antibiotic-mediated inhibition of cellular metabolism, whereas high viral replication biologically demonstrates Mtb drug resistance. Finally, this phage-based drug resistance detection assay is a biological test as it directly measures the biological effect a drug has on tuberculosis. While previous biological tests were growth based and took several weeks to identify a difference in bacterial growth between drug treated and untreated samples, FASTPLAQUE-RESPONSE™ is a rapid biological test that does not measure cell growth. Instead, it uses the mycobacteriophage D29 to measure an antimicrobial's effect on host cell metabolism. Although an accurate and rapid test, FASTPLAQUE-RESPONSE™ is too complicated and unwieldy for use in resource-poor settings because the analysis of viral growth by plaque formation on agar plates must be performed in a laboratory by a highly-trained technician.

Another phage-based system for the detection of Mtb drug resistance measures the enzymatic activity of a single phage-encoded polypeptide rather than the ability of the entire mycobacteriophage to replicate and spread as is done by FASTPLAQUE RESPONSE™. This system was originally developed by researchers at Albert Einstein College of Medicine and is known as the Luciferase Reporter Assay (LRA). The LRA utilizes a recombinant version of the mycobacteriophage TM4 that has been engineered to highly express the luciferase gene from the firefly *Photinius pyralis*. Luciferase is a single subunit enzyme that, upon cleavage of its substrate luciferin in the presence of ATP and molecular oxygen, releases a photon of light. The presence of luciferase can thus be measured by detecting its light production. During Luciferase Reporter Phage (LRP) infection of untreated Mtb, the luciferase polypeptide accumulates and its enzymatic activity can be detected by measuring photon production after adding luciferin, which readily enters Mtb cells. Incubation of drug susceptible Mtb with appropriate anti-tuberculosis antibiotics either kills the cell outright or leads to a decrease in the metabolic capacity of the cell. Because adenosine triphosphate (ATP) is the essential source of potential energy in the bacteria and luciferase activity requires ATP for not only enzyme activity but also for the luciferase enzyme's synthesis, luciferase activity is an indicator of a bacteria's metabolic capacity and hence the effect a given anti-microbial has on bacterial viability. During LRP infection of drug susceptible Mtb treated with an anti-tuberculosis antibiotic, luciferase enzyme synthesis and subsequent light production is dramatically reduced compared to an LRP infected control to which no anti-tuberculosis antibiotic was added. This differential in luciferase activity demonstrates an antimicrobial's effectiveness against Mtb. However, if light production in drug-treated and LRP infected Mtb is similar to an untreated control, the Mtb isolate is identified as drug resistant. The LRA has been evaluated in clinical trials testing Mtb resistance to first line anti-microbials and shown to have greater than 90% sensitivity and 100% specificity. Although an excellent tool to speed detection of drug resistant Mtb, only very sophisticated luminometers can detect luciferase light production from the small numbers of bacteria present in a clinical specimen. The LRA is thus not amenable to use in resource-poor settings that do not have the capacity to purchase and operate a high quality luminometer.

Recent efforts to rapidly identify drug resistance directly from clinical specimens employ nucleic acid amplification (NAA) to detect specific Mtb genomic loci that confer resistance to commonly used anti-tuberculosis drugs. NAA is a process by which a nucleic acid sequence is selectively replicated using enzymatic methods to increase the number of identical nucleic acid sequence molecules and thereby increase the sensitivity of the assay. Many but not all examples of nucleic acid testing (NAT) use NAA. NAT is the detection of nucleic acids using methods such as molecular binding, hyrbidization, fluorescence, chemiluminescence, and radioactivity to specifically or non-specifically detect nucleic acids. One example of a NAT that employs NAA is Hain Lifescience's (Nehren, Gennany) GENOTYPE® MtbDR, which uses a line probe assay to detect specific drug resistance alleles amplified from clinical sample-derived Mtb DNA. GENOTYPE® MtbDR is proving very complicated and expensive as there are over 15 commonly observed known mutations that confer resistance to RIF and INH.

Another molecular diagnostic technology in development by Cepheid (Sunnyvale, Calif.) is intended only for diagnosis of RIF resistance in Mtb. Cepheid's market advantage is mostly due to the GENEXPERT® system, which fully automates sample processing and NAA. However, detection of the individual resistance loci in the amplification reaction requires fluorescent probes that are expensive to synthesize and require sophisticated detection hardware. Because of this limitation, the Cepheid product is limited to detecting the five major mutations involved in RIF resistance. For the Cepheid system, simultaneous detection of both RIF and INH resistance loci would be too unwieldy and expensive.

All currently available molecular diagnostic technologies fail to satisfy today's need for effective diagnostics as they are incapable of detecting Mtb strains that are RIF or INH resistant but harbor uncharacterized mutations. They also fail to identify isolates resistant to other first-line antibiotics, much less XDR-TB strains, because the full gamut of clinically relevant mutations conferring resistance to all anti-Tb drugs is not known. A rapid molecular diagnostic test able to identify all drug-resistant Mtb strains, including emergent XDR-TB, will be an important and necessary tool for the effective treatment and control of drug-resistant tuberculosis. The development of such rapid molecular testing technology would also be relevant and important for other diseases including, but not limited to, cholera, cryptosporidiosis, leishmaniasis, meningitis, and pneumonia. Additionally, the development of accurate molecular testing enabling the detection of microbes would also be useful for the detection of contaminants in pollutants ranging in sample type from drinking water to laboratory reagents.

What are needed are effective diagnostic and therapeutic tools to address the ever persisting and ever evolving challenges posed by infectious disease, in particular mycobacterial disease. In addition, as the use of antibiotics becomes increasingly widespread, and in some cases where the use of antibiotics is not in compliance with prescribed and recommended regimens, we find ourselves challenged with novel strains of infectious agents and microbes that no longer respond to standard therapies. What is needed therefore, are effective tools for identifying infectious agents, wherein such tools are also preferably capable of determining drug susceptibility. Importantly, what is needed are diagnostic tools that are easy to use, that require minimal testing time, and that are inexpensive so that they are readily available for use in parts of the world where the disease is prevalent, and where resources are limited.

What are also needed are efficient, simple and accurate molecular testing technologies that enable the detection of infectious agents, that provide information concerning the viability of the infectious agent and that determine drug susceptibility. Use of such technologies would not be limited to infectious disease alone; their utility could be extended to detection and evaluation of microbes and pollutants in a variety of samples ranging from biological to industrial.

SUMMARY OF THE INVENTION

The present invention comprises novel molecular constructs, devices, systems, and methods for the detection and identification of microbes and infectious agents. In addition to detecting infectious agents, the present invention may be used to determine important infectious agent and microbe characteristics such as viability, metabolic state, and drug susceptibility.

In one aspect, the present invention comprises novel nucleic acid constructs or surrogate marker locus (SML) generation modules. The SML is a nucleic encoded universal marker of cell viability or metabolism. The SML generation module comprises a source of nucleic acid or nucleotide modifying activity and in certain embodiments, a source nucleic acid sequence on which the source of nucleic acid or nucleotide modifying activity acts to generate the SML. In certain exemplary embodiments the source of nucleic acid or nucleotide modifying activity is a nucleic acid modifying polypeptide. In one exemplary embodiment, the polypeptide is a DNA or RNA polymerase. In another exemplary embodiment, the polypeptide is a DNA or RNA recombinase. In certain other exemplary embodiments, the source of nucleic acid modifying activity is a catalytic nucleic acid. In one exemplary embodiment, the catalytic nucleic acid is a RNA cyclase ribozyme. In another exemplary embodiment, the catalytic nucleic acid is a group II intron. In certain other embodiments, the SML generation module comprises a combination of polypeptide and catalytic nucleic acid activity. In one exemplary embodiment, the SML generation module comprises both RNA polymerase and RNA cyclase ribozyme.

The composition of the source nucleic acid sequence will vary depending on the source of nucleic acid modifying activity to which it is paired. In general, the source nucleic acid will comprise a recognition site for the enzymatic activity of the polypeptide or catalytic nucleic acid and one or more defined signature tag sequences to which a corresponding primer or oligonucleotide primer can bind. The signature tag sequences are designed so that they cannot be detected or amplified until after generation of the SML. Regardless of the particular SML generation module design used, the SML is not detectable or amplifiable until generated by the enzymatic function of the SML generation module. The SML may comprise DNA, RNA, or a combination thereof.

The SML generation module may be encoded within a vector. The vector may be viral or non-viral. For non-viral vectors, delivery to a microbe may be facilitated by standard transfection technologies such as electric pulsing, electroporation, osmotic shock, and polymeric-based delivery systems (5). In one exemplary embodiment the vector is a bacteriophage. In certain exemplary embodiments, the vector is a mycobacteriophage.

In one exemplary embodiment the SML generation module is encoded within a bacteriophage genome and comprises a sequence encoding a RNA polymerase under the transcriptional control of a promoter known to function in the target microorganism. The SML generation module further comprises a source nucleic acid sequence inserted into a transcriptionally silent locus of the bacteriophage genome. The source nucleic acid is located downstream and under the transcriptional control of a promoter specific to the encoded RNA polymerase. In certain exemplary embodiments, the source nucleic acid may further comprise a transcription termination sequence.

In another exemplary embodiment, the SML generation module is encoded within a bacteriophage genome and comprises a sequence encoding a recombinase under the transcriptional control of a promoter known to function in the target microorganism and a source nucleic acid comprising two recombinase-specific recognition sites, or recombination substrates, and two signature target sequences located between the recombination substrates. In one exemplary embodiment, the recombinase is a Cre recombinase, Flp recombinase, or a serine phage integrase. In certain exemplary embodiments the components of the recombinase-based SML generation module are contained on separate vectors, with the recombinase encoded on a first vector and the source nucleic acid sequence encoded on a second vector. In other exemplary embodiments, the components of the recombinase-based SML generation module are encoded on a single vector. In one exemplary embodiment, the recombinase is a Bxb1 integrase, the source nucleic acid comprises an attP recombination sequence and an attB recombination sequence and one or more signature tag sequence encoded between the attB and attP sequences.

In another exemplary embodiment, the SML generation module is encoded within a bacteriophage genome and comprises a nucleic acid sequence encoding a RNA polymerase under the transcriptional control of a promoter known to function in the target microorganism and a source nucleic acid under the transcriptional control of a promoter specific to the RNA polymerase. The source nucleic acid comprises two halves of a sequence that encodes the RNA cyclase ribozyme (6) and two signature tag sequences located between the RNA cyclase ribozyme halves.

In another exemplary embodiment, the SML generation module is encoded within a bacteriophage genome and comprises a group II intron sequence and an Intron Encoded Protein (IEP). In certain exemplary embodiments, the bacteriophage genome encodes a IEP under the control of a first promoter, a group II intron sequence lacking its internal IEP under the control of a second promoter, a first and second exon sequence, wherein a first copy of the first and second exon sequence flank either end of the group II intron sequence, and an inverted second copy of the first and second exon sequence are located adjacent to each other and upstream of the second promoter. In one exemplary embodiment, the IEP is LtrA from the L1.1trB intron from *Lactococcus lactis* and the group II intron sequence is the L1.1trB intron with the LtrA open reading frame deleted (L1.1trBΔLtrA). In certain other exemplary embodiments the IEP is encoded within the group II intron sequence and under the control of a single promoter.

In certain exemplary embodiments, the SML generation modules are designed to incorporate a capture or isolation aptamer sequence into the SML. An aptamer is a nucleic acid sequence with specific and predictable binding characteristics. In certain exemplary embodiments the aptamer is capable of binding to a solid matrix or solid support or components attached thereto. In one exemplary embodiment, the aptamer is a streptavidin-binding aptamer. In another exemplary embodiment, the aptamer is a cellulose binding aptamer.

In another aspect, the present invention is directed to methods of generating SMLs in a cell comprising introducing into the cell a SML generation module, wherein the SML generation module contains a source of nucleic acid or nucleotide modifying function. Upon successful introduction into the cell, the source of nucleic acid or nucleotide modifying function generates, de novo, a distinct SML from a source nucleic acid. In certain exemplary embodiments, the source nucleic acid is further encoded in the SML generation module. In another exemplary embodiment, the SML is generated from a source nucleic acid within the host.

In another aspect, the present invention is directed to methods of using the SML generation modules described above to determine information regarding an infectious agent or microbe's pathogenic state. For example, the methods of the present invention can be used to assess the identity of a microbe, whether the microbe is viable, whether the microbe is metabolically active or dormant, and whether the microbe is susceptible to certain anti-microbial compounds.

In one exemplary embodiment, a method of determining the viability of a microbe comprises (1) incubating a test sample with a SML generation module, wherein expression of a polypeptide or catalytic nucleic acid of the SML-generation module generates, de novo, a distinct SML, and (2) detecting generation of the SML, wherein detection of the SML indicates the infectious agent is viable. In certain exemplary embodiments, the SML generation module is introduced into the microbe by a vector encoding the SML generation module. Where the vector is specific for the infectious agent or microbe, detection of the SML can also identify the infectious agent or microbe present. In certain exemplary embodiments, multiple vectors, each specific for a different infectious agent or microbe, and each encoding SML-generation modules designed to generate distinct SMLs, may be used to identify and determine the viability of multiple infectious agents or microbes in a sample. In certain exemplary embodiments the vector encoding the SML generation module is a bacteriophage. In other certain exemplary embodiments, the incubation step further comprises the application of electric pulsing, electroporation, or osmotic shock.

In another exemplary embodiment, the above method further comprises a step of assessing the microbe's metabolic state by determining a microbe genomic marker level. Suitable genomic markers of an infectious agent or microbe include, but are not limited to, rRNA, the genes that encode for rRNA and other loci encoded in the genome of the infectious agent or microbe. Detection of the SML indicates the microbe is viable and comparison to the level of a genomic marker of the microbe provides information on the microbe's metabolic state. Detection of genomic marker levels lower than detected SML levels indicates the microbe is viable and highly metabolically active. Detection of genomic marker levels comparable to or higher than detected SML levels indicates the microbe is viable but dormant. In the situation where a patient has begun antibiotic therapy, comparison of SML generation to the genomic locus standard determines the metabolic capacity of the microbe and hence the efficacy of the therapy administered to the patient.

In yet another exemplary embodiment, the method of determining viability may comprise exposing the test sample to a drug or drug combination prior to incubating the test sample with a SML generation module. Robust detection of the SML indicates the microbe(s) remain viable in the presence of the drug or drug combination, whereas failure to detect or low levels of SML indicates the microbe(s) are susceptible to the drug or drug combination. The embodiment may further comprise the use of a control sample run in parallel and without exposure to the drug or drug combination to further verify the results. In yet a further exemplary embodiment, a sample may be split into a series of reaction vessels and each tested with a SML-generation module which generate a distinct SML, following testing, the samples can be pooled for further processing (sample multiplexing). The results unique to each reaction vessel can be identified by the distinct SML generated during or after testing. A specific embodiment of this process would allow splitting a patient isolate into a series of antibiotics, and following incubation, the samples could be pooled for SML detection to identify the antibiotic sensitivity profile of the patient sample.

The methods of the present invention can be used to assess the pathogenic state of a wide range of infectious agents including, but not limited to, bacterial, mycological, and parasitic agents. In one exemplary embodiment, the methods are used to assesses the pathogenic state of a *Mycobacterium*. In yet another exemplary embodiment, the methods are used to assess the pathogenic state of one or more of *M. tuberculosis, M. avium-intracellulare, M. kansasii, M. fortuitum, M. chelonae, M. leprae, M. africanum, M. microti, M. avium paratuberculosis, M. intracellulare, M. scrofulaceum, M. xenopi, M. marinum*, and *M. ulcerans*. In yet another exemplary embodiment, the methods of the present invention are used to assess the pathogenic state of *M. tuberculosis*.

The methods of the present invention can be used to assess a number of sample types including body fluid samples, industrial samples, or environmental samples. Representative biological samples include, but are not limited to, sputum, tears, saliva, sweat, mucus, serum, urine, or blood. Representative industrial samples include, but are not limited to chemical reagents, culture media, innocula, cleaning solutions, and swabs of solid surfaces. Representative environmental samples include drinking water, samples from a natural body of water, including fresh and marine bodies of water, samples from recreational waters, including water parks, swimming pools, whirlpools, hot tubs and spas. In one exemplary embodiment, the sample is minimally processed sputum.

The SMLs generated during the incubation stage can be isolated using standard nucleic acid isolation and purification methodologies known in the art including but not limited to agarose and/or acrylamide gel purification methods, phenol/chloroform extractions, column purification based methods and liquid chromatography, and assays that use sequence-specific hybridization or affinity to a solid matrix. The SMLs generated during the incubation step may be detected using suitable nucleic acid detection technology. Suitable nucleic acid detection technologies include, but are not limited to, hybridization-based assays, polymerase chain reaction (PCR)-based assays, nucleic acid sequence based amplification (NASBA)-based assays, and transcription mediated amplification-based assays (TMA). In one exemplary embodiment detection of the SML is carried out on a lateral flow assay device.

BRIEF DESCRIPTION OF THE FIGURES

FIG. 2A shows a representative prior art genotyping assay, which requires the complicated analysis of multiple microbial genomic loci. FIG. 2B provides a schematic of an exemplary streamlined process for determining drug susceptibility using the SML technology of the present invention.

FIG. 3A shows a representative prior art genotyping assay, which requires the complicated analysis of multiple microbial genomic loci. FIG. 3B provides a schematic of an exemplary streamlined process for determining multiple-drug resistance using the SML technology of the present invention.

DETAILED DESCRIPTION

Figure 1:
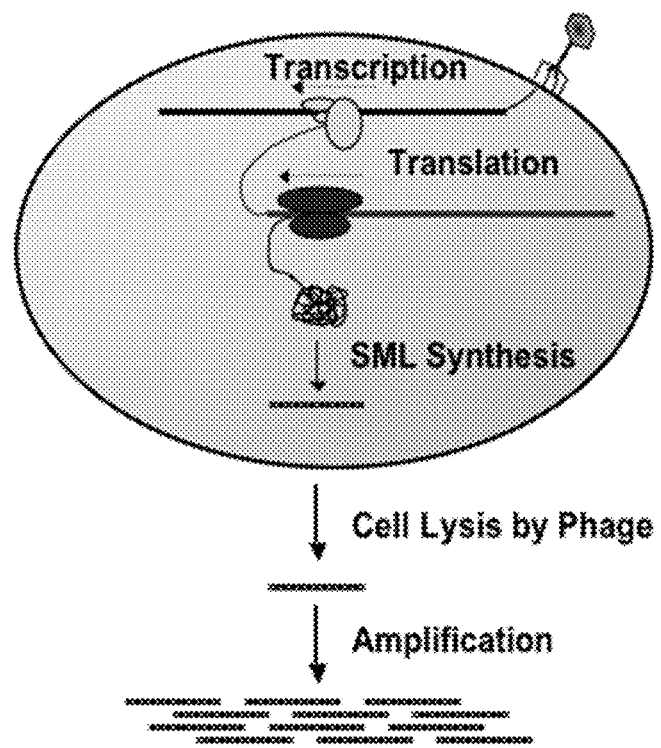
FIG. 1 provides a schematic of an exemplary SML generation process. Upon infection of a viable microbe, expression of the polypeptide or catalytic nucleic acid encoded in the SML generation module leads to SML synthesis. The SML can then be isolated and detected using standard nucleic acid amplification technologies.

The present invention may be understood more readily by reference to the following detailed description of the specific embodiments included herein. However, although the present invention has been described with reference to specific details of certain embodiments thereof, it is not intended that such details should be regarded as limitations upon the scope of the invention. The entire text of the references mentioned herein are hereby incorporated in their entireties by reference including U.S. Provisional Patent Application Ser. No. 60/922,213, filed Apr. 5, 2007, U.S. Provisional Patent Application Ser. No. 60/927,287, filed May 1, 2007, U.S. Provisional Patent Application Ser. No. 60/927,217, filed May 2, 2007, U.S. Provisional Patent Application No. 61/297,056 filed Jan. 21, 2010, and U.S. Provisional Patent Application No. 61/371,646 filed Aug. 6, 2010.

The present invention comprises a platform of novel molecular constructs, devices, systems, and methods for detecting and assessing the pathogenic state of a microbe. As used herein "pathogenic state" refers to information concerning a microbe's viability, metabolic state and drug susceptibility. The platform is built around the generation of a surrogate marker locus (SML), which is a nucleic acid encoded universal marker of cell viability. The present invention can provide information on a microbe's drug susceptibility profile without any prior knowledge of the genetic changes that encode drug resistance in a particular microbe. For most microbes, the present invention can provide simultaneous reporting of microbial identification and pathogenic state in a matter of hours rather than days or weeks. Additionally, the present invention is fully automatable and amenable to multiplexing.

Surrogate Marker Locus Generation Modules

The SML is generated by novel nucleic acid constructs or surrogate marker locus (SML) generation modules. The constructs encode specific nucleic acid modifying functions which can generate, de novo, a new and distinct nucleic acid sequence or SML from a source nucleic acid upon successful introduction into a microbe. Polypeptides, catalytic nucleic acids or other means to reliably and predictably generate a new nucleic acid sequence may provide the nucleic acid or nucleotide modifying function. The SML is generated from a source nucleic acid sequence that may be encoded within the construct itself or derived from source nucleic acid sequences within the microbial host. In one exemplary embodiment, the SML is generated from a source nucleic acid encoded within the construct itself. The composition of the source nucleic acid sequence may vary depending on the type of enzymatic activity used to generate the SML. For example, if the enzymatic activity is a RNA polymerase, the source nucleic acid may encode a short artificial transcript under the control of a promoter specific to that RNA polymerase. In the context of the present invention, artificial transcripts refers to a RNA sequence, typically between 50 bp and 3000 base pairs, that would not be present except for its generation by the nucleic acid or nucleotide modifying function encoded by the SML generation module. In other instances, the source nucleic acid may comprise an intervening sequence located between recombination substrates, splice sites, or other sites of nucleic acid modifying activity. The source nucleic acid may include one or more signature tag sequences to which corresponding primers or oligonucleotides can bind to the SML for detection and amplification. Tag sequences can vary in length from approximately 15 base pairs to approximately 50 base pairs. The target sequences are designed so that they cannot be detected or amplified until after generation of a SML. Regardless of the particular SML generation module design used, the SML is not detectable until generated by the nucleic acid or nucleotide modifying function of the SML generation module.

The SML generation modules are encoded in a vector. The vector may be a viral or non-viral based vector. For non-viral vectors, the SML generation modules may be delivered intracellularly to microbes by standard transfection technologies such as electric pulsing, electroporation, osmotic shock, and polymeric-based delivery systems (7). In one exemplary embodiment, the SML generation module is encoded in a non-viral vector. Suitable non-viral vectors include, but are not limited to, plasmids, phasmids, bacterial artificial chromosomes, yeast artificial chromosomes, cosmids, linear double stranded DNA, linear single stranded DNA, circular single stranded DNA, linear double stranded RNA, linear single stranded RNA, circular single stranded RNA, circular double stranded RNA, linear RNA and DNA hybrids and circular RNA, DNA hybrids and complexes consisting of, but not limited to, nucleic acids and proteins. In another exemplary embodiment the SML generation module is encoded in a bacteriophage (SML-phage). The bacteriophage may be specific for one or more bacterial genera or species. In another exemplary embodiment the bacteriophage is specific to *Mycobacterium*. In yet another exemplary embodiment, the bacteriophage is specific to *M. tuberculosis*. In another exemplary embodiment the bacteriophage is a TM4-based mycobacteriophage. In another exemplary embodiment the bacteriophage is a DS6a-based mycobacteriophage or any other mycobacteriophage whose host range is restricted to members of the TB Complex.

Enzymatic polypeptides that may be used in the SML generation modules of the present invention include those polypeptides with nucleic acid modifying functionality. In one exemplary embodiment, the polypeptide is a DNA recombinase, a RNA recombinase, a RNA polymerase, a DNA polymerase, a transcription factor, a sigma factor, a DNA methylase, a DNA demethylase, a DNA restriction endonuclease, a DNA ligase, a RNA ligase, a histone acetylase, a histone deacytlase, a uridine deaminase, a reverse transcriptase or a RNA maturase. In another exemplary embodiments, the polypeptide is a DNA or RNA polymerase. Suitable polymerases for use with the present invention include, but are not limited, to SP6 RNA Polymerase. In another exemplary embodiment, the polypeptide is a recombinase. Suitable recombinases for use with the present invention include, but are not limited to, Cre, Flp, or serine phage integrases.

In certain embodiments, the SML generation module encodes an enzymatic nucleic acid. In one exemplary embodiment, the catalytic nucleic acid is a RNA cylcase, ribozyme, a group I intron, a group II intron, a riboswitch, a gene regulation ribozyme, or RNase P. Gene regulation ribozymes that may be used with the present invention include hammerhead, hairpin, HDV, and VS ribozymes. In one exemplary embodiment, the catalytic nucleic acid is a RNA cyclase. In another exemplary embodiment, the catalytic nucleic acid is a group II intron.

Polymerase-Based SML Generation Modules

Figure 13:
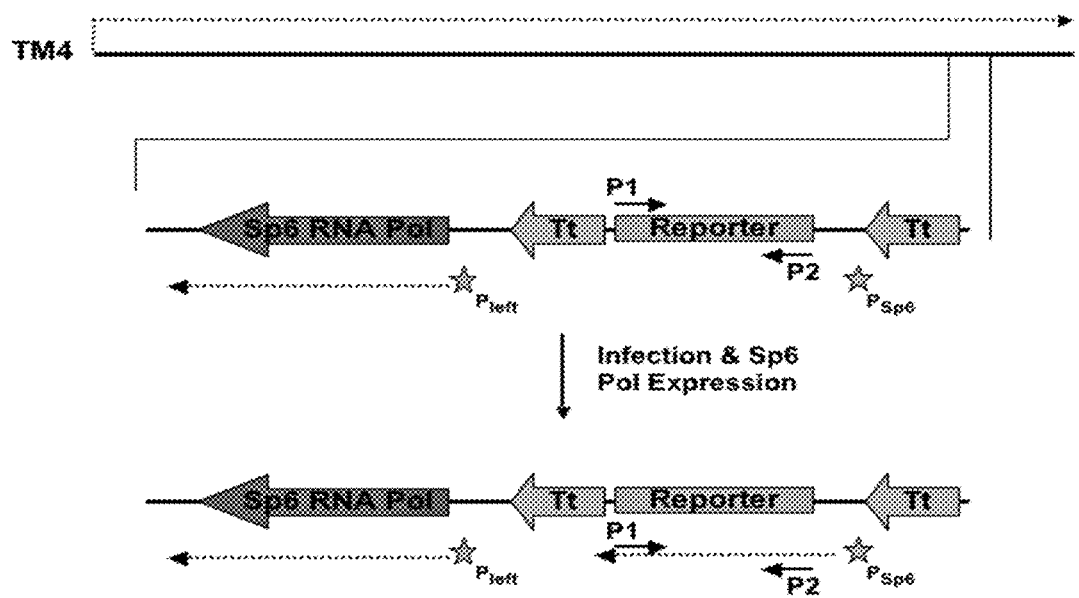
FIG. 13 is a schematic showing the genetic structure of an exemplary Sp6 RNA polymerase-based SML generation module.

In one exemplary embodiment the SML generation module is encoded within a bacteriophage genome and comprises a sequence encoding a RNA polymerase under the control of a promoter known to function in the target microorganism. The SML generation module further comprises a source nucleic acid sequence inserted into a transcriptionally silent locus of the bacteriophage genome. The source nucleic acid is located downstream and under the transcriptional control of a promoter specific to the encoded RNA polymerase. The RNA polymerase is expressed from the bacteriophage promoter upon successful introduction into a microbe and can initiate transcription of the source nucleic acid sequence downstream of the encoded RNA polymerase promoter. The generation of RNA polymerase-dependent transcripts constitute generation of the SML. In one exemplary embodiment, the bacteriophage is a TM4 mycobacteriophage, the RNA polymerase is a Sp6 RNA polymerase under the transcriptional control of a mycobacteriphage L5 $P_{left}$ promoter and the RNA polymerase-specific promoter is a Sp6 promoter. FIG. 13 depicts the genetic structure of this SML generation module. The transcriptional direction of endogenous phage genes is depicted by the dashed arrow at the top of the figure. The Sp6 RNA polymerase is expressed by the mycobacteriophage L5

$P_{left}$ promoter (grey star) on the strand opposite that of endogenous TM4 gene transcription. Upstream of Sp6 RNA polymerase is the Sp6 consensus promoter (orange star) and the reporter sequence flanked by two transcription termination sites (Tt). Sp6-dependent transcription of the reporter sequence constitutes generation of the SML, and can be detected by nucleic acid amplification technologies using primers P1 and P2.

Recombinase-Based SML Generation Modules

In another exemplary embodiment, the SML generation module is encoded within a bacteriophage genome and comprises a sequence encoding a recombinase under the transcriptional control of a bacteriophage-specific promoter and a source nucleic acid comprising one or more signature tag sequences located between two recombinase-specific recognition sequences, or recombination substrates. Primers or probes are designed to the signature tag sequences within the source nucleic acid. In one exemplary embodiment, there are two signature tag sequences. The signature tag sequences are oriented within the source nucleic acid sequence so that their corresponding primers would be oriented in opposite directions and therefore unable to generate a PCR product prior to SML generation.

In one exemplary embodiment, the bacteriophage encodes, in a 5' to 3' direction, a first recombination substrate, a first signature tag sequence, a recombinase, a second signature tag sequence, and a second recombination substrate. The recombinase is expressed from the bacteriophage promoter upon successful introduction into a microbe and mediates recombination between the first recombination substrate and the second recombination substrate. The reaction generates a small circular DNA molecule containing the first and second signature tag sequences. This molecule constitutes generation of the SML and results in the primers corresponding to the signature tag sequences being oriented in an opposed position allowing for the generation of a PCR product. In one exemplary embodiment, the recombinase is a Bxb1 integrase, the first recombination substrate is an attP sequence and the second recombination substrate is an attB sequence. There are three characteristics that make Bxb1 integrase and similar enzymes effective SML generation enzymes. Bxb1 is derived from a bacteriophage and therefore is likely to exhibit full activity during bacteriophage infection of target microbe cells. However, this characteristic does not preclude its use in other non-viral vectors. Indeed Bxb1 integrase has been shown to be active in many types of cells ranging from *Mycobacteria* and *Plasmodia* to mammalian cells. The Bxb1 recombination substrates contain only one eight base pair repeat, (8) helping to eliminate the frequency of illegitimate recombination events. The Bxb1 integrase is negatively regulated by the Bxb1 Xis polypeptide. This facilitates creation of a single SML generation module with both integrase and the SML source nucleic acid in the same vector. This is particularly useful in the context of phage-based vectors because expression of Xis in trans from the host cell genome during growth of phage stocks can help to preclude integrase-mediated SML generation.

Figure 12:
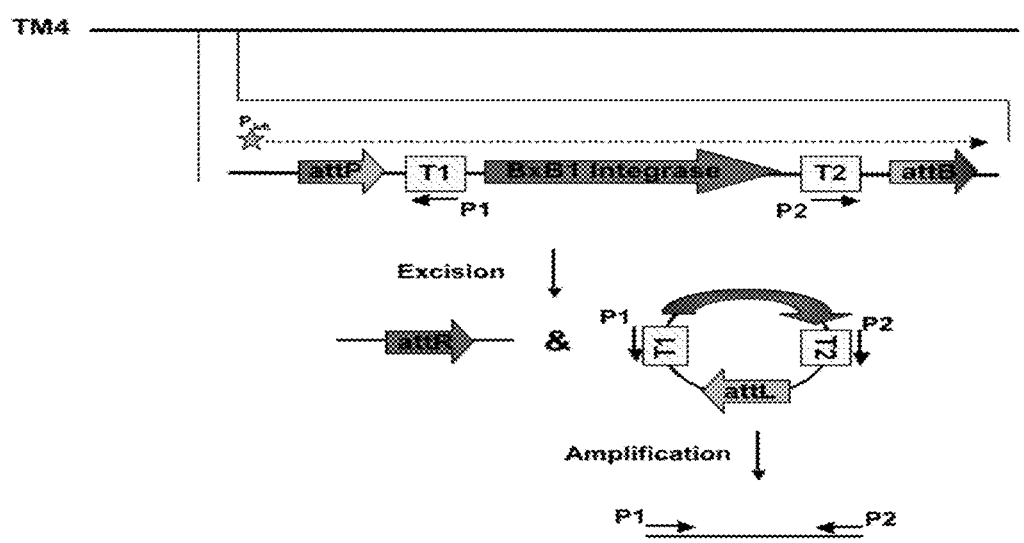
FIG. 12 is a schematic showing an exemplary genetic structure and generation of a SML using a Bxb1 integrase-based SML generation module.

Integrase-based SML generation modules exploit the ability of integrase to mediate recombination between attP and attB sites. As illustrated in FIG. 12, SML-modules can be created by inserting a nucleic acid sequence encoding the integrase (Int), along with attP and attB sites into a suitable vector under the control of a vector based promoter such as the $P_{left}$ promoter. Primers P1 and P2 can be designed to bind to signature tag sequences (T1 and T2) placed on either side of the Int, and adjacent to the attP and attB sites. P1 and P2 are oriented in opposite directions and are unable to generate a PCR product. Expression of Int from the $P_{left}$ promoter in viable, metabolically active microbes leads to recombination between attP and attB sites. This reaction generates two products: 1) a new site attR in the vector; and 2) a small circular DNA molecule containing the Int gene, T1, T2, and a new site, attL. This molecule constitutes generation of the SML, as P1 and P2 are now opposed and can generate a PCR product. Furthermore, because the SML product is circular, it is highly stable and resistant to degradation.

Ribozyme-Based SML Generation Modules

In one exemplary embodiment, the SML generation module is encoded within a bacteriophage genome and comprises a nucleic acid sequence encoding a RNA polymerase under the transcriptional control of a bacteriophage-specific promoter and a source nucleic acid under the transcriptional control of a promoter specific to the RNA polymerase. The source nucleic acid comprises two halves of a sequence that encodes the RNA cyclase ribozyme(9). After expression of the RNA Polymerase, RNA is synthesized that contains one half of RC (RC1) on the 5' end of the source nucleic acid and the other half of RC (RC2) on the 3' end of the source nucleic acid. Once synthesized, the RC elements in the source nucleic acid mediate circularization. In addition, the RC RNA sequences fuse to each other as a byproduct. Circularization of the source nucleic acid sequence results in a new RNA sequence that is distinct from the cognate DNA locus in the SML generation module and constitutes generation of the SML. As in the recombinase embodiment above, target nucleic acid sequences within the source nucleic acid sequence can be defined so that their corresponding primers are oriented opposite to each other and cannot generate a PCR product from the SML's cognate DNA locus. Circularization results in the primers being oriented towards each other on the circular SML allowing them to mediate amplification of the intervening RNA sequence. See FIG. 24. This facilitates the use of all amplification technologies capable of using RNA as a substrate to detect SML generation and helps rule out false positives from the cognate DNA locus in the SML generation module.

Intron-Based SML Generation Modules

In another exemplary embodiment, the SML generation module is encoded within a bacteriophage genome and comprises a group II intron sequence and an Intron Encoded Protein (IEP). Group II introns are selfish DNA elements capable of inserting into DNA at specific sites. Generally, they interrupt protein-coding regions of genomic DNA and are removed post-transcriptionally to regenerate the open reading frame (ORF). Splicing of many Group II introns requires the maturase activity of the IEP. In addition to maturase activity, IEPs often exhibit endonuclease and reverse transcriptase (RT) activities. Once synthesized, the IEP binds the intron RNA and stabilizes its secondary structure to accomplish two goals. The first is splicing of the intron RNA to fuse the exon sequences and regenerate a complete ORF in the messenger RNA. The second is insertion of the intron RNA into an "intron-less" allele of the ORF in the cell genome. The insertion of the intron sequences into an intron-less allele is called retrohoming and results in the re-creation of the same intron-exon junctions of the previous intron-interrupted allele. Once the intron RNA is inserted into the intron-less allele, it must be converted into DNA to become a permanent fixture of the cell genome. For many Group II introns, this is accomplished by the reverse transcriptase activity of the IEP.

In certain exemplary embodiments, the bacteriophage genome encodes a IEP under control of a first promoter, a source nucleic acid sequence encoding a group II intron sequence under the control of a second promoter, a first and second exon sequence, wherein a first copy of the first and second exon sequence flank either end of the group II intron sequence, and an inverted second copy of the first and second exon sequence are located adjacent to each other and upstream of the second promoter. In one exemplary embodiment, the IEP is LtrA from the L1.trb intron from *Lactococcus lactis* and the group II intron sequence is the L1.1trB intron with the LtrA open reading frame deleted.

Figure 25:
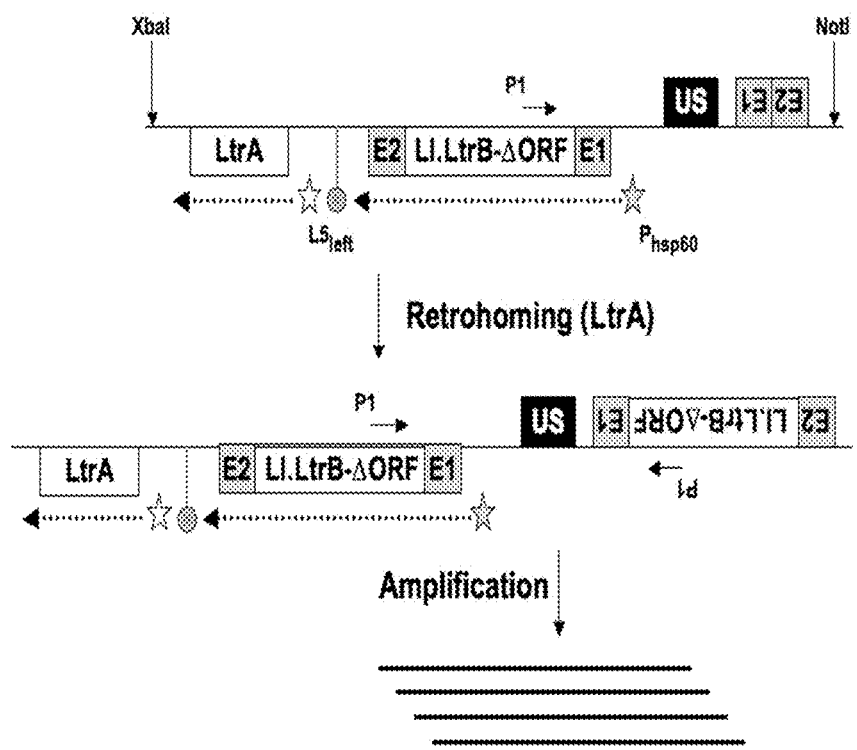
FIG. 25 is a schematic of an exemplary genetic structure of a Group II intron-based SML generation module.
Figure 26:
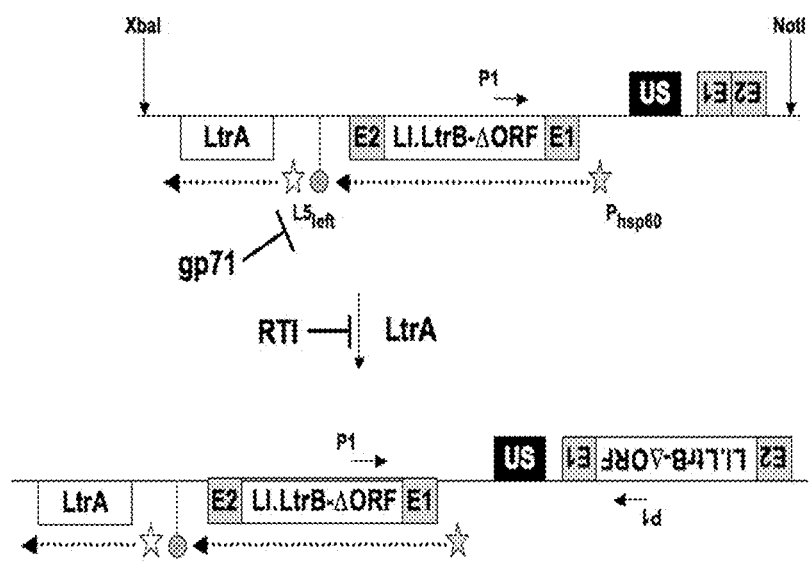
FIG. 26 is a schematic demonstrating how bipartite control of retrohoming can be obtained on Group II intron-based SML generation modules.

As depicted in FIG. 25, the intron RNA (L1.1trBΔORF) may be transcribed by host RNA polymerase from the constitutive $P_{hsp60}$ promoter and is terminated at a downstream transcription termination site in order to not interfere with expression of LtrA from the $P_{left}$ promoter. When both $P_{hsp60}$ and $P_{left}$ are active, the two elements required for retrohoming, namely, the L1.1trBΔORF RNA and LtrA, accumulate, and a copy of L1.1trBΔORF is inserted into a target site (inverted E2E1) placed upstream of $P_{hsp60}$. Once L1.1trBΔORF is inserted into the target site and reverse transcribed, two binding sites for primer P1 exist. Furthermore, as illustrated in FIG. 25, the E1E2 target site is in reverse orientation compared to E1 and E2 fused to L1.1trBΔORF under $P_{hsp60}$ transcriptional control, and directs the insertion of the L1.1trBΔORF intron into the target site in reverse orientation. This results in the P1 binding sites being oriented towards each other such that P1 can generate an amplification product consisting of the intervening sequence. Without retrohoming of L1.1trBΔORF into the target site, there is only one binding site for primer P1 and thus amplification cannot occur. In certain other exemplary embodiments the IEP is encoded within the group II intron sequence and under the control of a single promoter. Retrohoming can be controlled by inhibiting both expression of LtrA and its RT activity. As illustrated in FIG. 26, expression of LtrA from the $P_{left}$ promoter will be downregulated by expression in trans of the mycobacteriophage L5 gp71 polypeptide from the host cell genome. Gp71 is a potent inhibitor of transcription elongation from $P_{left}$. Cell lines that constitutively express gp71 exist and have been used to downregulate expression of transgenes incorporated into reporter mycobacteriophage under $P_{left}$ transcriptional control. However, transcriptional inhibition by gp71 is not absolute and some LtrA is synthesized. To preclude retrohoming by the residual amount of LtrA that accumulates, cells containing the L1.LtrB-based SML generation module may be incubated with a small molecule RT inhibitor (RTI) that exhibits sufficient activity against LtrA. By controlling both LtrA expression and RT activity, it is possible exert control over retrohoming and SML synthesis.

Another advantage of employing L1.1trB or any other similar Group II intron, is that specific bases in L1.1trB and the exon sequences can be altered to direct retrohoming to alternative sites. It may be possible to target L1.1trB to a new site such that after retrohoming, the inserted copy of L1.1trB is flanked by recombinase binding sites, which in the presence of the recombinase, remove and circularize the inserted L1.1trB. This results in the recreation of the L1.1trB homing site to facilitate a second insertion event. This strategy would allow the SML generation system to make many copies of the SML, and, once created, the SML would not be part of the SML generation module. This would facilitate removal of the SML from the SML-phage preparation to ensure there is no carryover into a test for bacterial viability or drug resistance.

Incorporation of Aptamer Sequences in SMLs to Facilitate Purification

A key step in diagnostics that employ nucleic acid amplification is the purification of target nucleic acids away from amplification inhibitors derived from the test sample. Another concern is amplification of target nucleic acids that constitute a minute minority of total nucleic acid in the sample. This is especially problematic when highly conserved sequences such as ribosomal RNA are the targets. Ideally, the target nucleic acid is selectively purified away from other nucleic acids, as well as amplification inhibitors. Approaches such as sequence-specific capture using biotinylated oligonucleotides attached to a solid support like streptavidin-coated paramagnetic beads are routinely employed to selectively purify and concentrate target nucleic acids prior to amplification. Although effective, sequence specific capture using oligonucleotides is complex since the target nucleic acids often must first be denatured to melt secondary structure and allow the oligonucleotide to hybridize to its complement present in the target.

Figure 24:
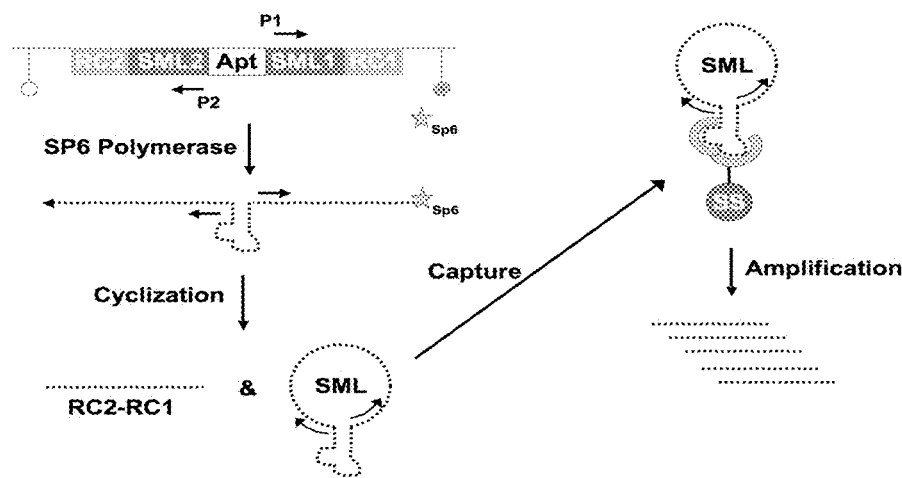
FIG. 24 is a schematic showing how the use of aptamer sequences can be used to simplify selective purification of the SML RNA.

To address this issue, the source nucleic acids of the SML generation module can be designed to encode an aptamer that has the ability to bind solid matrixes or solid supports or components attached thereto. The aptamer can be used in conjunction with any SML generation module design, but by way of example an embodiment showing the use of an aptamer in a RNA Cyclase Ribozyme-based generation is depicted in FIG. 24. A sequence that encodes a RNA aptamer (Apt) known to bind with high affinity to a solid support (SS) such as streptavidin coated paramagnetic beads, is inserted into the SML generation module in an internal position of the source nucleic acid that encodes two signature tag sequences (SML1 and SML2), which is, in turn, internal to the two halves of the RNA Cyclase Ribozyme (RC1 and RC2). The Apt, SML1&2 and RC1&2 elements are downstream of the SP6 promoter. Primers P1 and P2 hybridize to SML1 and SML2 and are oriented such that they cannot produce an amplification product using the SML generation module as a substrate. After transcription of the locus by SP6 RNA Polymerase, a linear RNA is synthesized that possesses the aptamer. Once RC2 is synthesized and correctly folded, a circular RNA is produced that contains the Aptamer, and SML1 and SML2 fused together. To purify and concentrate the fused SML, a SS is added to which the Aptamer binds. Following purification, it may be possible to amplify the SML RNA using P1 and P2 while it is attached to the SS through Apt. In one exemplary embodiment, the aptamer is a streptavidin binding aptamer or a cellulose binding aptamer.

Methods for Determining Viability, Metabolic State, and Drug Susceptibility

In addition to providing a universal reporter for microbe detection and identification, the present invention also provides useful information regarding the pathogenic state of a microbe as SML generation depends on viable and functional microbe for its production. Therefore detection of the SML indicates the microbes being tested are viable, unlike other nucleic acid based assays which can still detect nucleic acids present from dead or lysed microbes in the sample. When incubating a microbe with a SML generation module in the presence of a drug composition, the SML platform can be used to conduct drug susceptibility testing. Failure to detect a SML indicates the microbe is susceptible to the drug composition tested, whereas detection of the SML indicates the microbe is resistant. It is also useful to know whether a detected microbe is active and virulent, or weather the microbe is dormant. The SML platform can provide this information by including a step of detecting a metabolic marker of the microbe.

The primary steps a method of determining the viability of a microbe comprises (1) incubating a test sample with a vector encoding SML-generation module, wherein expression of a polypeptide or catalytic nucleic acid of the SML-generation module generates de novo a distinct SML, and (2) detecting generation of the SML, wherein detection of the SML indicates the infectious agent is viable. Where the vector is specific for the infectious agent or microbe, detection of the SML can also identify the infectious agent or microbe present.

The present invention can be further used to assess a microbe's relative level of metabolic activity, ranging from dormant to active. Detection of the SML indicates the microbe has sufficient metabolic capability to support SML synthesis and a genomic sequence encoded by the microbe provides information on the number of microbes in the sample. A comparison to the metabolic activity and number of micro-organisms demonstrates the metabolic activity of the microbe population in the sample. Suitable genomic markers of an infectious agent or microbe include, but are not limited to, rRNA, the genes that encode for rRNA and other loci present in the genome of the infectious agent or microbe. Detection of genomic marker levels lower than detected SML levels indicates the microbe is viable and capable of causing infection, or virulent. Detection of genomic marker levels comparable to or higher than detected SML levels indicates the microbe is viable but dormant. In this manner, the number of infectious organisms in a sample and the metabolic activity of the microbes can be ascertained. Applying this method to a patient sample could ascertain the direct metabolic effect of an antibiotic administered to the patient upon a pathogen in the patient sample.

To assess a microbe's drug susceptibility profile, the method of determining viability is modified to include a step of exposing the test sample to a drug or drug combination prior to incubating the test sample with a SML-generation module. Detection of the SML indicates the microbe(s) remain viable in the presence of the drug or drug composition, whereas significant reduction in SML generation or failure to detect SML indicates the microbe(s) are susceptible to the drug or drug combination. The embodiment may further comprise the use of a control sample run in parallel and without exposure to the drug or drug combination to further verify the results.

The methods of the present invention can be used to assess the pathogenic state of a wide range of microbes including, but not limited to, bacterial, mycological, and parasitic agents. The methods of the present invention may be used to assess the pathogenic state of bacteria including, but not limited to, *Bordetella, Bacillis, Borrelia, Brucella, Campylobacter, Chlamydia, Clamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Vibrio,* and *Yersinia*. The present invention may also be used to assess the pathogenic state of important bacterial indicators of environmental contamination such as fecal coliforms and hydrogen-sulfide producing bacteria. The present invention may be used to assess the pathogenic state of fungi including, but not limited to *Candida, Aspergillus, Cryptococcus, Histoplasma, Pneumocystis,* and *Stachybotrys*. The present invention may be used to assess the pathogenic state of protozoa including, but not limited to, *Entamoeba histolytica, Dientamoeba fragilis, Giardia lamblia, Trichomonas vaginalis, Balantidium coli, Naegleria fowleri, Acanthamoeba, Plasmodium falciparium, P. malariae, P. ovale, P. vivax, Isospora belli, Cryptosporidium parvum, Cyclospora cayetanensis, Enterocytozoon nieneusi, Babesia microti, Toxoplasma gondii, L. donovani, L. tropica, L. braziliensis, Trypanosoma gambiense, T. rhodesiense, T. cruzi,* and *Penumocystis jiroveci*. The present invention may be used to assess the pathogenic state of nematodes including, but not limited to, *Enterobius vermicularis, Ascaris lumbricoides, Toxocara canis, Toxocara cati, Baylisascaris procyonis, Ancylostoma duodenale, Necator americnaus, Strongyloides stercoralis, Ancylostoma braziliense, Trichuris trichiura, Trichinella spiralis, Wuchereria bancrofti, Brugia malaya, Loa boa, Onchocerca volvulus, Dracunculus medinensis, Capillaria philippinensis*. The present invention may be used to assess the pathogenic state of trematodes including, but not limited to *Fasciolopsis buski, Fasciola hepatica, Opisthorchis sinensis, Paragonimus westermani, P. kellicotti, Schistosoma mansoni, S. japonicum,* and *S. haematobium*. The present invention may be used to assess the pathogenic sate of cestodes including but not limited to, *Taenia solium, T. saginata, Diphyllobothrium latum, Dipylidium caninum, Echinococcus granulosis, E. multilocularis,* and *Hymenolepis nana*.

In one exemplary embodiment, the methods are used to assessed the pathogenic state of a *Mycobacterium*. In yet another exemplary embodiment, the methods are used to assess the pathogenic state of one or more of *M. tuberculosis, M. avium-intracellulare, M. kansasii, M. fortuitum, M. chelonae, M. leprae, M. africanum, M. microti, M. avium paratuberculosis, M. intracellulare, M. scrofulaceum, M. xenopi, M. marinum,* or *M. ulcerans*. In yet another exemplary embodiment, the methods of the present invention are used to assess the pathogenic state of *M. tuberculosis*.

The methods of the present invention can be used to assess a number of sample types including body fluid samples, industrial samples, or environmental samples. Representative biological samples include, but are not limited to, sputum, tears, saliva, sweat, mucus, serum, urine, or blood. Representative industrial samples include, but are not limited to chemical reagents, culture media, innocula, cleaning solutions, and swabs of solid surfaces. Representative environmental samples include drinking water, samples from a natural body of water, including fresh and marine bodies of water, samples from recreational waters, including water parks, swimming pools, whirlpools, hot tubs and spas. In one exemplary embodiment the test sample is sputum. In certain exemplary embodiments, the sputum may be liquified using a reducing agent, such as NALC, hypertonic saline, or cetylpyridinium chloride.

The methods of the present invention may also be used to assess the therapeutic efficacy of a drug or drug combination. A SML generation module may be delivered in vivo or in vitro to a disease tissue or cell line representative of a diseased tissue during or after its exposure to a given drug or drug combination. Detection of the SML indicates the cells remain viable in the presence of the drug or drug composition, whereas significant reduction in SML generation or failure to detect SML indicates the cells are susceptible to the drug or drug combination. In one exemplary embodiment the diseased tissue is a tumor. In another exemplary embodiment, the cell line is a cancer cell line. In one exemplary embodiment, the SML generation module is inserted into a virus that selectively replicate cancer cells. This SML-virus can then be used to detect the presence of cancer cells in a biopsy sample or in culture and determine the susceptibility of the cancer cells to a given anti-cancer drug or drug combination. The methods can be used to screen potential anti-cancer drugs or determine which anti-cancer drug or drug combination will be most effective against a patient's cancer.

The SML technology of the present invention can also be used as markers of biological phenomena that are not easily detected or measured. SML generation modules can be incorporated into bacterium, yeast, protozoa, fungi, or any other cultured cell. Generation and detection of the SML can be used to replace current research methods that measure, for example the enzymatic cleavage of chromogenic substrates (e.g. lacZ) or employ fluorescent or other light emitting proteins to measure the phenotypes of cells, The SMLs generated during incubated stages can be isolated using standard nucleic acid isolation and purification methodologies known in the art including, but not limited to, agarose and/or acrylamide gel purification methods, phenol/chloroform extractions, column purification based methods and liquid chromatography, and assays that use sequence-specific hybridization or affinity to a solid matrix. Where used, phage based vectors have the added of advantage of lysing the microbial cells avoiding the need for a separate lysing step. The SMLs generated during the incubation step may be detected using nucleic acid amplification (NAA). NAA is a process by which a nucleic acid sequence is selectively replicated using enzymatic methods to increase the number of identical nucleic acid sequence molecules and thereby increase the sensitivity of the assay. Many but not all examples of nucleic acid testing (NAT) use NAA. Suitable detection methods for use with the present invention also include those methods that do not rely on amplification, such as molecular binding, hyrbidization, fluorescence, chemiluminescence, and radioactivity to specifically or non-specifically detect nucleic acids. Suitable nucleic acid detection technologies include, but are not limited to, hybridization based assays, polymerase chain reaction (PCR) based assays, nucleic acid sequence based amplification (NASBA) based assays, and transcription mediated amplification based methods (TMA).

PCR is the most utilized technique for amplifying target nucleic acids, but has several characteristics at odds with use in the developing world. The most important of these is its requirement for rapid and precise temperature cycling between 50° C.-95° C. The present invention, while applicable to current PCR-based techniques, is specifically designed to insert into other nucleic acid amplification technologies that do not require temperature cycling and also have better detection thresholds. Amplification technologies that do not require temperature cycling are referred to as isothermal nucleic acid amplification technologies. They are specifically formulated to amplify DNA or RNA at a single incubation temperature, and therefore are appropriate for the developing world because the instrumentation required to execute and analyze these reactions is significantly cheaper. In one exemplary embodiment, the SML is detected using NASBA or TMA.

Figure 19:
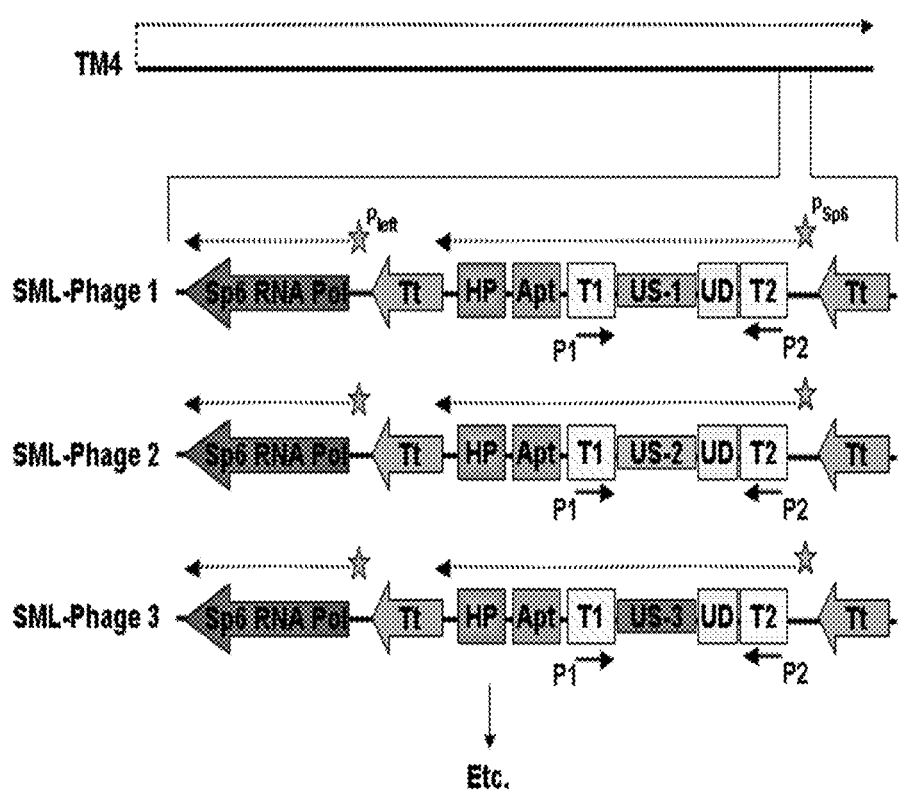
FIG. 19 is a schematic showing an exemplary genetic structure of multiple Sp6 RNA polymerase-based SML generation modules adapted for multiplexing and affinity based purification of SMLs.

In certain exemplary embodiments, the above methods can be carried out utilizing multiple SML generation modules in order to detect and assess the pathogenic state of multiple microbes simultaneously. An exemplary embodiment is shown in FIG. 19. The example shows a multiplex platform in the context of a RNA polymerase-based SML generation module encoded in a bacteriophage vector. However, other SML generation modules and vectors may be utilized following a similar design. Each vector, in this embodiment is a SML-phage, containing the following features: (1) unique sequences (US), which can be varied so that individual phage express different SMLs (US-1, US-2, US-3, etc.) so that different nucleic acid detection technologies can distinguish the SML by using distinct capture oligonucleotides that hybridize to the US region of the SML; (2) an optional hairpin (HP) structure at the 3' end of the SML to inhibit 3'-5' exonuclease degradation of the SML; (3) an optional isolation aptamer (Apt) sequence to facilitate isolation of the SML on solid supports, such as streptavidin coated paramagnetic beads; (4) signature tag sequence (T1 and T2) to which amplification primers (P1 and P2) bind. T1 and T2 can be common to all SML-phage so that only one primer pair is used in an amplification reaction; and (5) a universal detection sequence (UD) to which a reporter oligonucleotide coupled to a detectable marker (i.e. colloidal gold, latex beads, fluorophores, etc), wherein the reporter can hybridize to detect the SML and/or SML amplification products. Features (2), (3), and (5) are optional and can be selected based on the isolation and detection method used to detect the SML.

Figure 20:
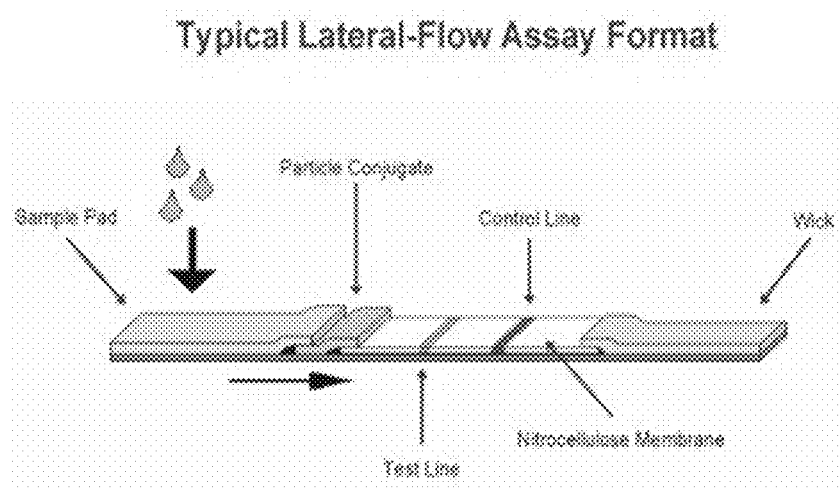
FIG. 20 is a schematic showing the general set up of a lateral flow assay that may be used to detect SMLs generated using the methods of the present invention.
Figure 21:
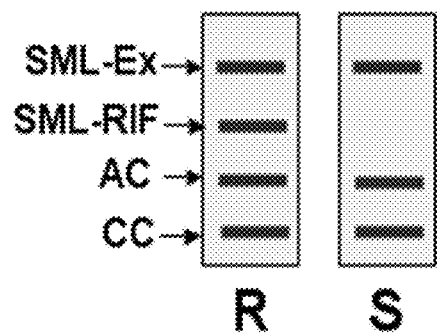
FIG. 21 is a schematic showing exemplary lateral flow assay readouts depicting both the detection of drug resistance and susceptibility. Detection of positive control SML (SML-EX), the test SML (SML-RIF), the amplification control (AC) and Conjugate Control (CC) is diagnostic of RIF drug resistance. Detection of SML-EX, AC, and CC but not SML-RIF is diagnostic of drug susceptibility.

In certain exemplary embodiments the detection step may be carried out on a lateral flow device. Lateral flow devices are well adapted for use with multiplex assays as described above. In addition, lateral flow detection can be an inexpensive method for the detection of nucleic acids and is suitable for deployment in peripheral laboratories in the developing world with minimal training of personnel. FIG. 20 shows the general set-up of a lateral flow assay. The exemplary flow devices comprise a sample pad, conjugate pad, analytical membrane and absorbent pad. Oligonucleotide probes designed to hybridize to the target sequences within the SML, such as the US sequences described above, can be bound to defined detection zones on the analytical membrane of the device In addition, where a UD sequence is employed a singled oligonucleotide polymer conjugated to a detectable marker can be used to detect bound SML on the analytical membrane. The detection oligonucleotide can be preloaded onto the particle conjugate pad. After isolation, a sample containing the SML is applied to the sample pad, which proceeds to wick onto the particle conjugate pad and is bound at the UD sequence by the detection oligonucleotide. The sample then proceeds to wick onto the analytical membrane where it will be captured by the fixed oligonucleotide probe corresponding to each SMLs unique target sequence. As the bound SML conjugates at the fixed detection site, a detectable line will appear indicating detection of the SML. FIG. 21 provides an exemplary readout of lateral flow assay assaying a microbe's susceptibility to RIF. Detection of a positive control SML (SML-EX), test SML (SML-RIF), an amplification control (AC) and conjugate control (CC) is diagnostic of RIF drug resistance. Detection of SML-EX, AC, and CC, but not SML-RIF is diagnostic susceptibility to the drug.

The following examples will illustrate the invention as it applies to the unique detection methods of the present invention. It will be appreciated that other examples, including minor variations in procedures and composition, will be apparent to those skilled in the art, and that the invention is not limited to these specific illustrated examples.

EXAMPLE 1

Figure 4:
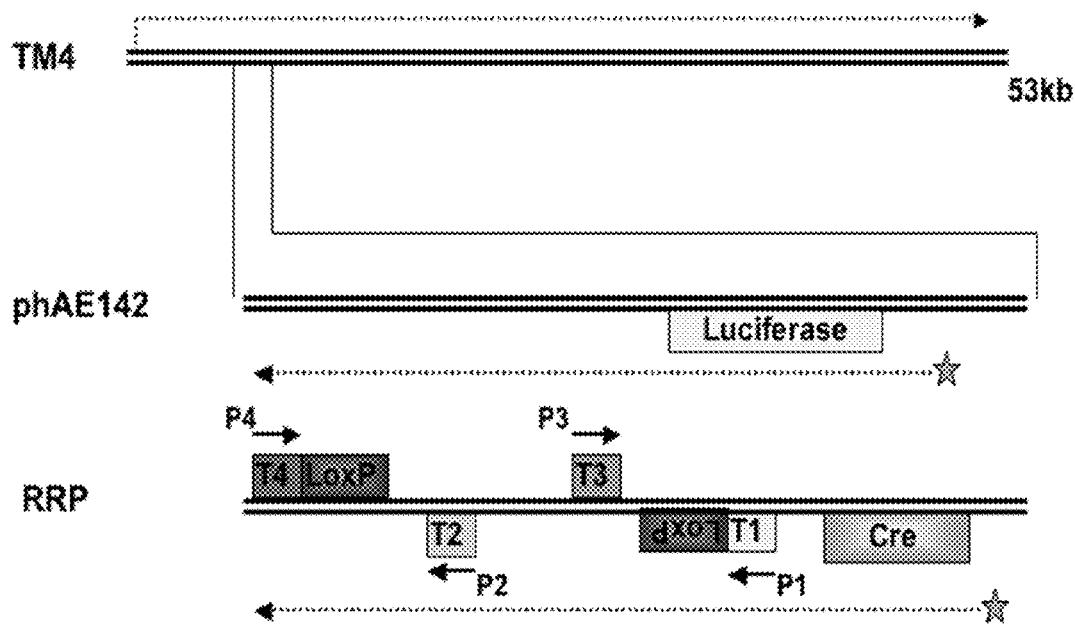
FIG. 4 is a schematic depicting an exemplary embodiment of a Cre recombinase-based SML generation module of the present invention.
Figure 5:
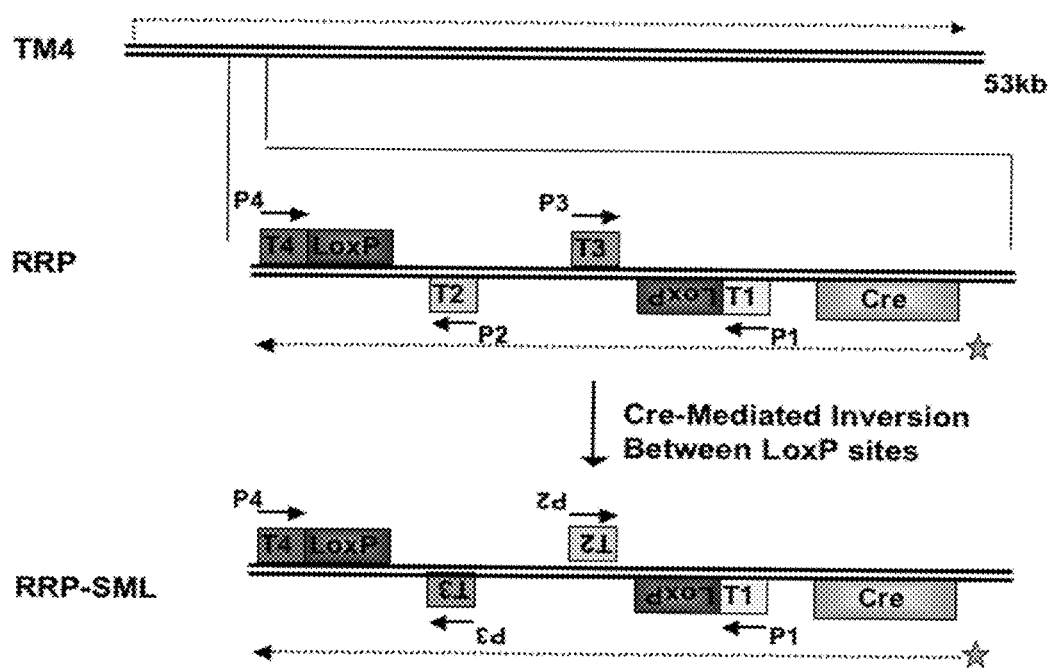
FIG. 5 is a schematic depicting an exemplary process by which a SML is generated through Cre recombinase facilitated inversion of loxP sites.

Mycobacteriphages Encoding Transcriptionally Regulated Cre Recombinase and Signature Tagged LoxP Sites The phAE142 is a TM4-based reporter phage which has been constructed to generate high levels of luciferase enzyme by placing its transcription under the control of the robust L5 Pleft promoter (Albert Einstein College of Medicine, Bronx, N.Y.). An additional advantage of this promoter is that it is exquisitely silenced by the L5 gp71 polypeptide, thereby negating the toxic effects of luciferase to viral growth during preparation of high-titer stocks by using Mycobacterium smegmatis (M.smeg) host cells that constitutively express gp71. In the present invention, the luciferase open reading frame (ORF) of phAE142 is replaced with, for example, the Cre recombinase gene from bacteriophage P1 using established molecular biology techniques. Cre is under control of the P$_{left}$ promoter in order to prevent Cre-mediated generation of the SML during production of phage stocks. Two LoxP sites are also placed downstream of the Cre ORF. (FIG. 4). The Recombinase Reporter Phage (RRP) measures the metabolic activity of a mycobacterial cell during infection by directing the transcription and translation of the Cre recombinase which will subsequently bind the phage genome at the loxP sites and, because the loxP sites are oriented in opposition to one another, Cre will mediate inversion of the intervening DNA sequence. This inversion will change the DNA sequence of the phage genome, which constitutes generation of the SML. The SML can then be detected using primer pairs P1-P2 or P3-P4 using any NAA-based detection technology (FIG. 5).

Figure 6:
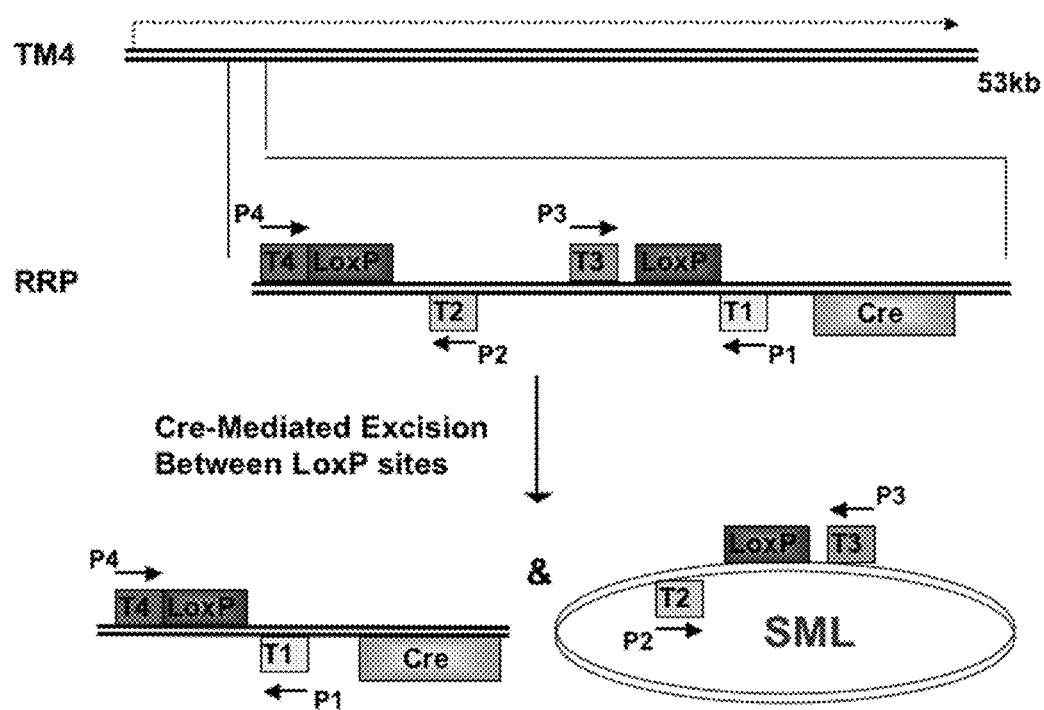
FIG. 6 is a schematic depicting an exemplary process by which a SML is generated through Cre recombinase facilitated excision of an intervening DNA sequence.

Arrangement of the loxP sites so that they are oriented in the same direction will lead to Cre-mediated excision of the intervening sequence rather than inversion. In this instance, the SML would be generated in an excised circular DNA molecule (FIG. 6). This strategy may be more amenable to RRP manufacturing as any spurious generation of the SML during growth of phage stocks will not be contained in the infectious phage genome because the SML is part of a circular DNA molecule with no cos sites for packaging into the phage head. This spurious SML can be easily removed form the phage stock by size exclusion chromatography or similar separation methods.

EXAMPLE 2

Novel Mycobacteriphage Transcription System for Identifying Antimicrobial-Resistant *Mycobacteria*

This example shows the rationale for an RNA-based SML reporter phage. This strategy employs the Sp6 RNA polymerase to generate an otherwise absent phage-encoded RNA. To accomplish this, the luciferase ORF of phAE142 is replaced with the Sp6 RNA polymerase from *Salmonella typhimirium* and is under P$_{left}$ transcriptional control. Additionally, the Sp6 promoter is integrated into an otherwise transcriptionally silent locus in the phage genome. Sp6-dependent RNA transcripts can then be detected using any NAA technology capable of detecting RNA.

Figure 7:
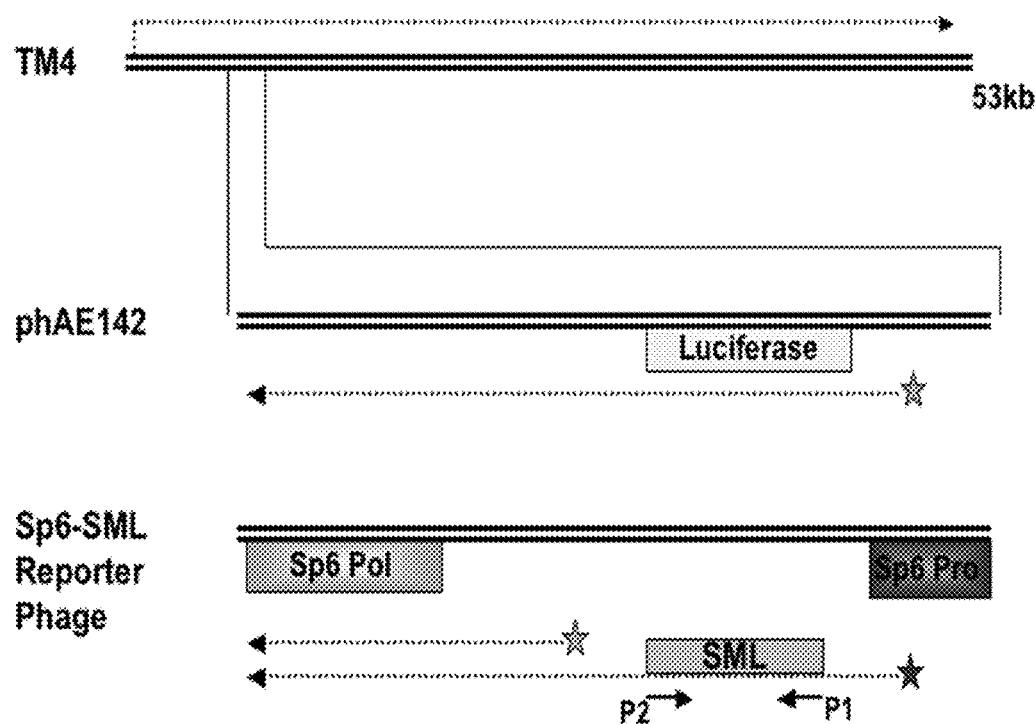
FIG. 7 is a schematic depicting an exemplary embodiment of a Sp6 RNA polymerase-based SML generation module of the present invention.
Figure 8:
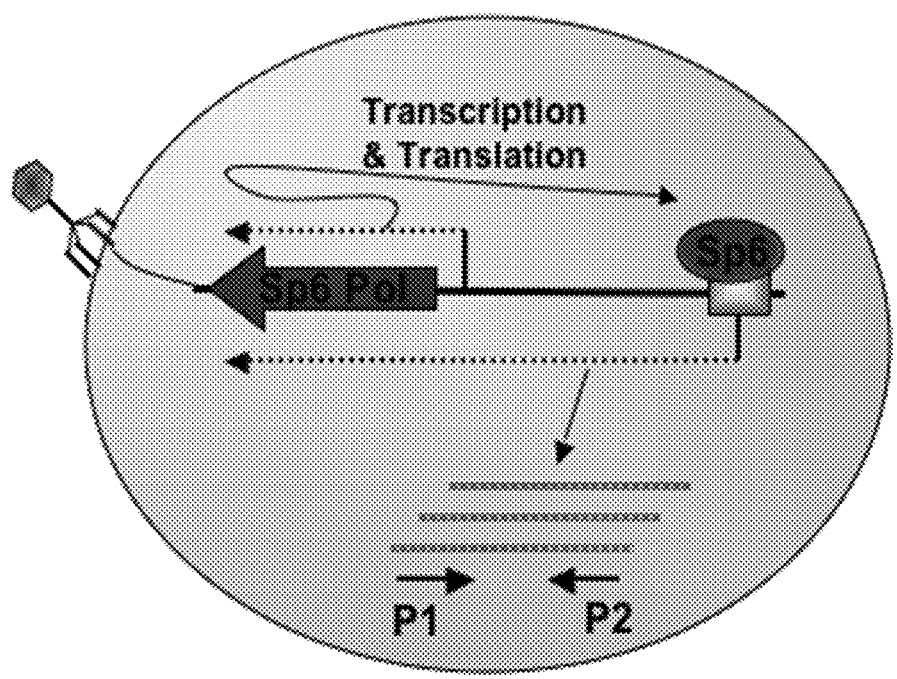
FIG. 8 is a schematic depicting an exemplary process by which a SML is generated through Sp6 facilitated transcription of source nucleic acid sequence.

RNA-Based SML Reporter Mycobacteriphage phAE142 is a TM4-based reporter phage. An advantageous feature of TM4 is that all of the known ORFs are contained on one strand of the double stranded genomic DNA and all are transcribed from a single promoter at one end of the genome (FIG. 7). Consequently, only one strand of phage RNA is transcribed during infection of *Mycobacteria*. Inclusion of the cognate DNA binding consensus sequence of a heterologues RNA polymerase into the phage genome in a transcriptionally silent locus renders that locus transcriptionally regulated by the heterologous RNA polymerase. Therefore, if the RNA polymerase is also integrated into the phage genome in a transcriptionally active locus, RNA transcription from the cognate promoter sequence should commence once the RNA polymerase is synthesized. In this formulation, RNA transcribed from the Sp6 promoter in an Sp6 RNA polymerase dependent fashion constitutes generation of the SML (see FIG. 8).

The following examples incorporate SML-phage technology of the present invention into Hain's genotype MTBDR test, an existing genetic test for Mtb drug resistance, in order to demonstrate how present invention simplifies molecular-genetic tests for drug resistance and how it can be expanded to detect resistance to any drug. Furthermore, other applications of the present invention for the detection of viable and drug resistant bacteria are illustrated. Either of the two types of SML reporter phages explained in the previous examples can be used in the following examples depending on which method of NAA is used: DNA or RNA-based (e.g. PCR or RT-PCR).

EXAMPLE 3

Figure 2:
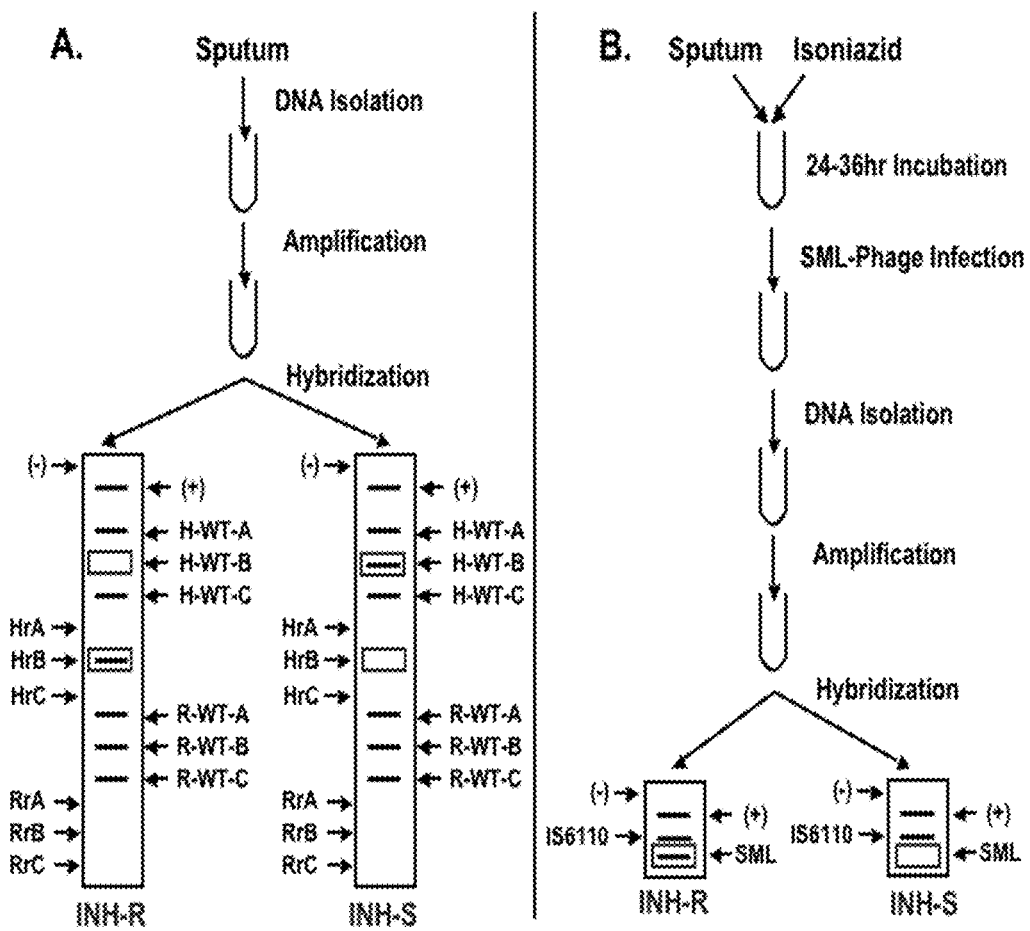
FIGS. 2A and 2B provide a comparative schematic demonstrating how the present invention can simplify the molecular detection of single drug resistance.

FIGS. 2A & 2B illustrate how SML-phage technology can be used to marry the accuracy of biological AST with the speed and sensitivity of NAA-based microbial detection methods. The Hain Lifescience GenoType-MTBDR test amplifies DNA isolated from a clinical specimen, in this case sputum, using primer sets specific for certain Mtb genes involved in resistance to both INH and RIF. Hain's core technology is the DNA-Strip: a line probe assay capable of discriminating single base substitutions in small pieces of DNA. After application of the amplification reaction products to the DNA-Strip, the products hybridize to completely homologous probe sequences immobilized on the DNA-Strip. This assay detects both the wildtype and mutant alleles of several mutations involved in resistance to RIF and INH. Although only three base substitution mutations involved in each form of drug ressatnce are shown in the figure, the actual Hain product is much more complicated as there are over 15 common individual point mutations involved in clinical resistance to both INH and RIF. FIG. 12A shows the general strategy for resistance mutation detection in the GenoType-MtbDR product. For Mtb to be identified as resistant to INH (INH-R) one of the mutant alleles conferring resistance to INH (HrB) must be detected while the corresponding WT allele (H-WT-B) must not be detected. If all WT alleles but none of the alleles involved in drug resistance are detected, then the isolate is identified as INH-susceptible (INH-S). SML generation technology can greatly simplify this system while expanding it to include detection of all clinical INH resistant strains by replacing all the WT and mutant alleles involved in drug resistance with the single SML. As shown in FIG. 12B, by incubating the sputum with INH for 24-36 hours and subsequently infecting Mtb with an SML-phage, detection of the SML after amplification diagnoses the presence of viable bacteria after incubation with INH. Because the phage was able to infect the bacteria and synthesize a phage-encoded polypeptide that mediates the creation of the SML, the bacteria are thus resistant to the effects of INH. As is clearly shown in FIG. 12, the advantage of the presently described SML-phage technology is that it is now possible for a biological assay of drug resistance to be analyzed through a simplified version of a current NAA-based molecular diagnostic technology.

Figure 3:
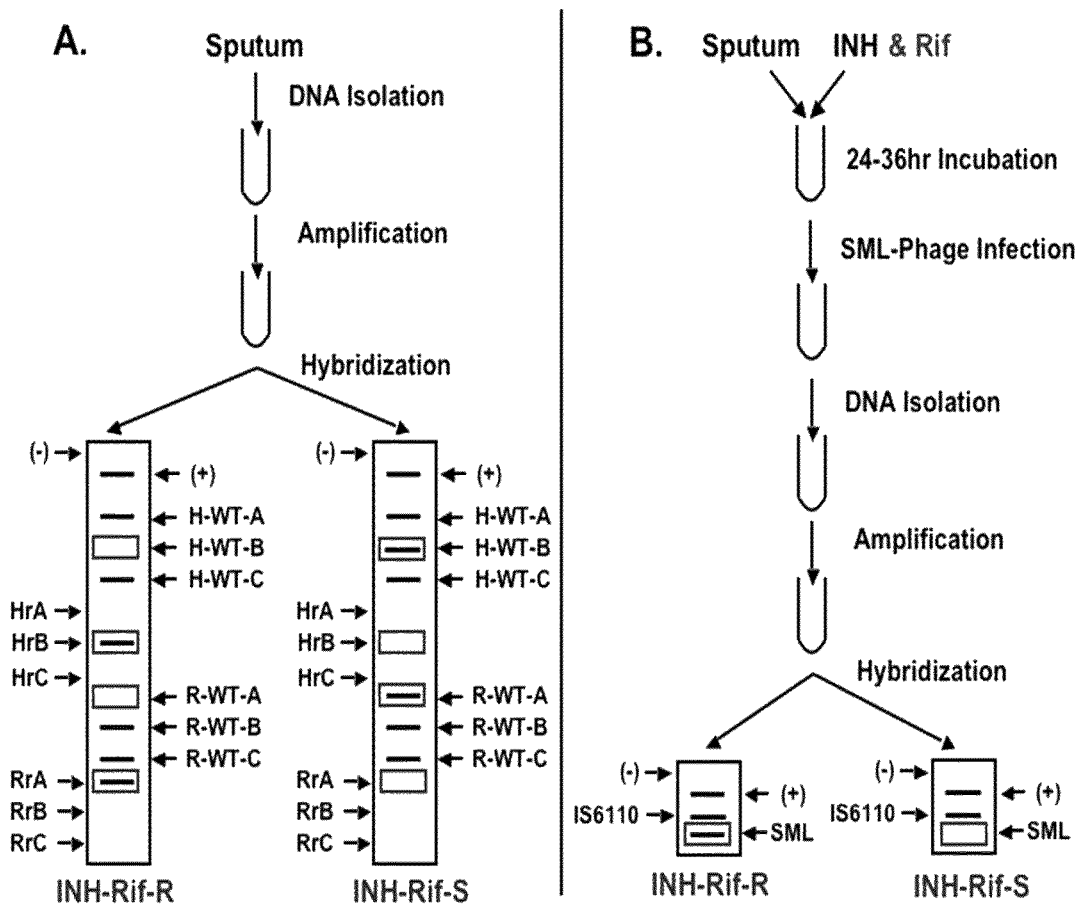
FIGS. 3A and 3B provides a comparative schematic demonstrating how the present invention can simplify the molecular detection of multiple drug resistance.

While Hain's Genotype MtbDR test cannot cover all instances of INH and RIF drug resistance, even with upwards of thirty loci analyzed using DNA-Strip, the present invention can test for resistance to any relevant drug by simply changing the antibiotic used to incubate Mtb isolated from a clinical sample. FIGS. 3A and 3B demonstrates how the present invention technology can be used to detect multi-drug resistant Mtb, which is defined as resistance to both RIF and INH. While Genotype MtbDR requires that two resistance associated alleles, one for INH and one for RIF must be detected along with the absence of the corresponding WT alleles, simply adding both INH and RIF together during incubation of Mtb prior to phage infection accomplishes the better goal of phenotypically demonstrating RIF and INH resistance rather than inferring it from small mutations in the Mtb genome. The biological detection of drug resistance, because it measures phenotype, not genotype, is inherently more accurate and comprehensive than individually detecting the most common resistance mutations observed in the clinic. Furthermore, Hain's DNA-Strip technology must differentiate single base pair hybridization differences while SML-phage technology simply requires the detection of wholly different segments of nucleic acid, an approach that is significantly less prone to hybridization artifacts. Moreover, the presently describe SML-phage technology allows for the rapid generation of new AST devices for detecting emergent drug resistance for new antimicrobials or for ones that little is known about the molecular-genetic bases for clinically relevant drug resistance.

The readout of the present invention for multi-drug resistance is the same as for single-drug resistance: SML synthesis. This allows the same NAA and detection system to be used for all products relating to Mtb drug resistance. This should dramatically lower the cost and difficulty in manufacturing individual tests for all permutations of Mtb drug resistance: MDR-TB test (INH and RIF resistance); Resistance to individual first line drugs (INH, RIF, Ethambutol, or Streptomycin); Resistance to individual second line drugs; XDR-TB test (INH, RIF, and key second line drugs)

Finally, because the SML generation module are transferable to any virus, either DNA or RNA-based, SML-phage technology can be used to detect drug resistance in any cell infected by a virus.

EXAMPLE 4

The Simultaneous Use of Multiple SML Phage to Determine which Viable Pathogenic Bacteria is in a Clinical Sample and which Antibiotic will Kill it in Order for the Physician to Initiate Proper Treatment Because SML-phage technology is transferable to any virus, multiple phages, each specific for a different geni or species of clinically relevant pathogen, can be generated. Each of these phage can synthesize either identical or unique SMLs and be incorporated into a device or system similar to the ones described here to generate a rapid biological AST that can be analyzed using established NAA and detection technologies. In other words, the full gamut of AST devices proposed for Mtb in this application could also be generated for any other bacteria so long as SML technology is transferable to a virus that infects the bacteria of interest.

Another application, which is not readily obvious, is to combine several SML-phage together into one infection vessel. Each SML-phage infects a different geni or species of bacteria and generates an identical SML after infection of a viable host bacteria. A device could be constructed that allows for a single clinical sample to be split evenly between several reaction chambers. Each chamber contains all of the phage but a different anti-microbial. This allows the physician to analyze the clinical sample in order to answer two very important questions: (1) Which viable pathogenic bacteria is present in the sample; and (2) Which antimicrobial will kill it and should therefore be prescribed to the patient?

Figure 9:
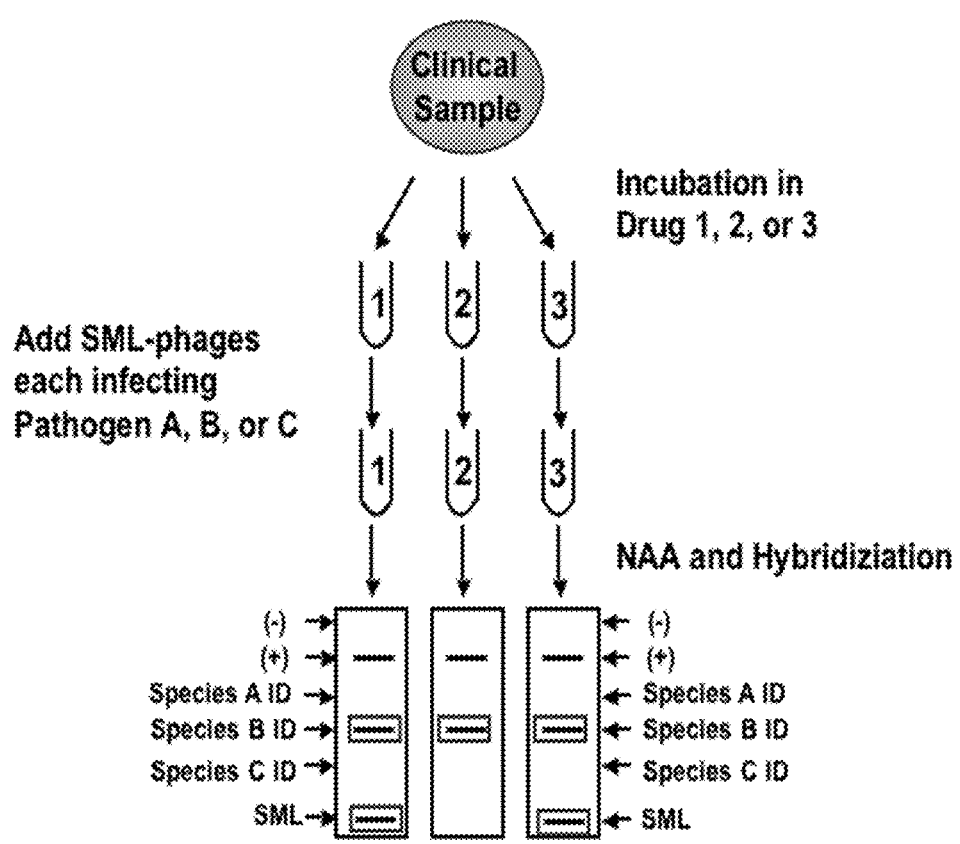
FIG. 9 is a schematic depicting an exemplary process wherein the drug susceptibility of multiple microbes is determined using multiple species-specific SML-phages.
Figure 10:
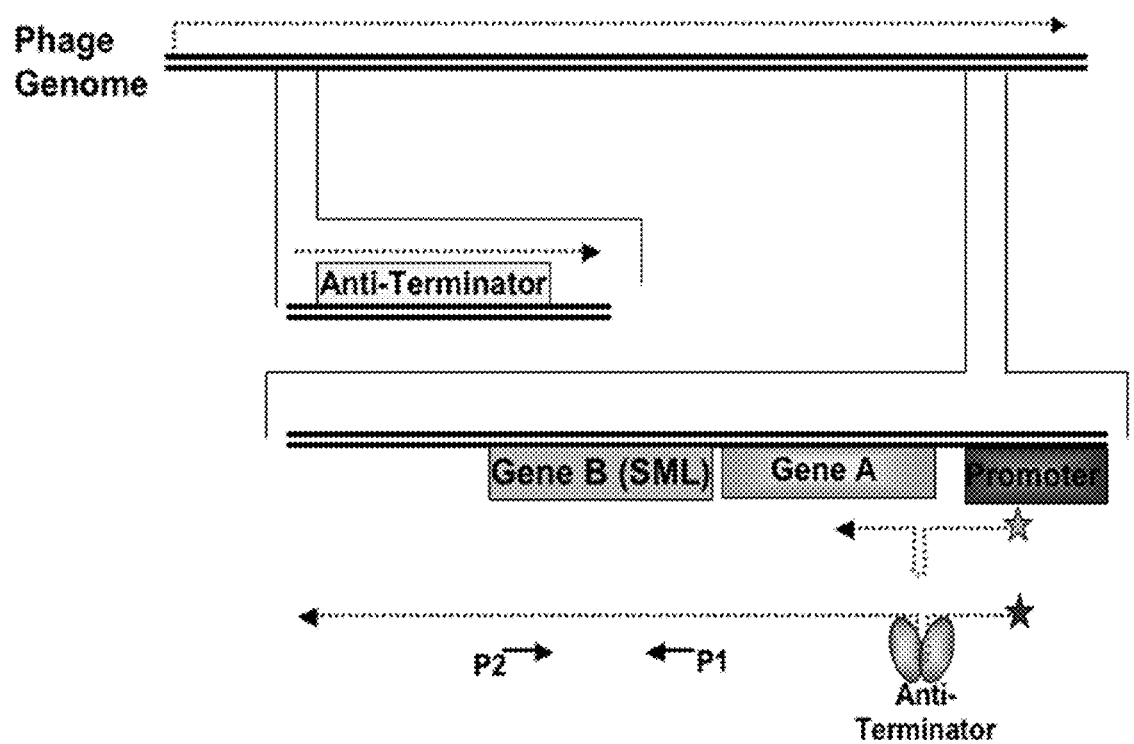
FIG. 10 is a schematic depicting a "naturally occurring" SML generation mechanism based on inherent bacteriophage transcriptional regulatory mechanisms.

FIG. 9 illustrates how such a system would be organized. There are various permutations upon this theme to increase specificity. Conversely one can combine a collection of phage specific to different bacteria to probe a sample for different bacteria. For example, each geni or species specific phage would generate a unique SML. A complete diagnostic result would include detection of both a positive species identification as well as the species-specific SML-phage SML so that there would be redundancy in the analysis to ensure accuracy. Also, several antimicrobials could be added to one vessel so that a cocktail of drugs could be prescribed for an extra confidence in successful treatment.

EXAMPLE 5

Use of Bacteriophage Transcriptional Regulatory Mechanisms for Detecting "Naturally Occuring" SMLs This example illustrates transcriptional regulatory mechanism in bacteriophage that can be used to detect "naturally occurring" SMLs. Many viruses exert temporal control over their gene expression programs. In other words, various functions exist to allow some genes to be expressed earlier in the infection than others and vice versa. Termination/anti-termination of phage transcription is a common mechanism to regulate the temporal expression of some genes. In this example, the mechanism is illustrated. In this example, all promoters are actively transcribed during the early phase of phage infection. For Gene A and Gene B, under control of their respective promoter, a mRNA transcript is synthesized, but a hairpin loop forms in the growing RNA polymer that destabilizes the transcription complex and leads to termination of the mRNA before it can fully transcribe, for example, Gene A as well as Gene B. However, as infection proceeds, transcription and translation of another gene, the anti-terminator, occurs relatively unimpeded. Accumulation of the anti-terminator polypeptide complex proceeds over time until it is able to bind the hairpin RNA of the transcript initiated at the promoter for Genes A and B. This polypeptide-RNA complex facilitates efficient elongation of the mRNA and transcription of the downstream, previously untranscribed, genes (e.g. GeneB). Because transcription of Gene B is dependent on the prior expression and synthesis of the anti-terminator, Gene B should not be transcribed during infection of non-viable cells or cells that have been exposed to an anti-microbial or other compound that inhibits cell viability and/or metabolism. Gene B, therefore, is an example of a "naturally occurring SML" in that decreases in cell viability through, for example, treatment of susceptible cells with an effective drug precludes or limits the transcription of Gene B and no exogenous functions need be engineered into the virus to generate an SML. Thus, detection via RNA-based NAA and detection technologies of Gene B anti-terminator regulated transcription serves as a surrogate resistance locus in a manner similar to that illustrated in Example 2.

Detection of any instance or mechanism of temporal regulation of phage transcription that reports on the drug susceptibility or viability of the cell can constitute detection of a SML or like viability locus.

EXAMPLE 6

Figure 11:
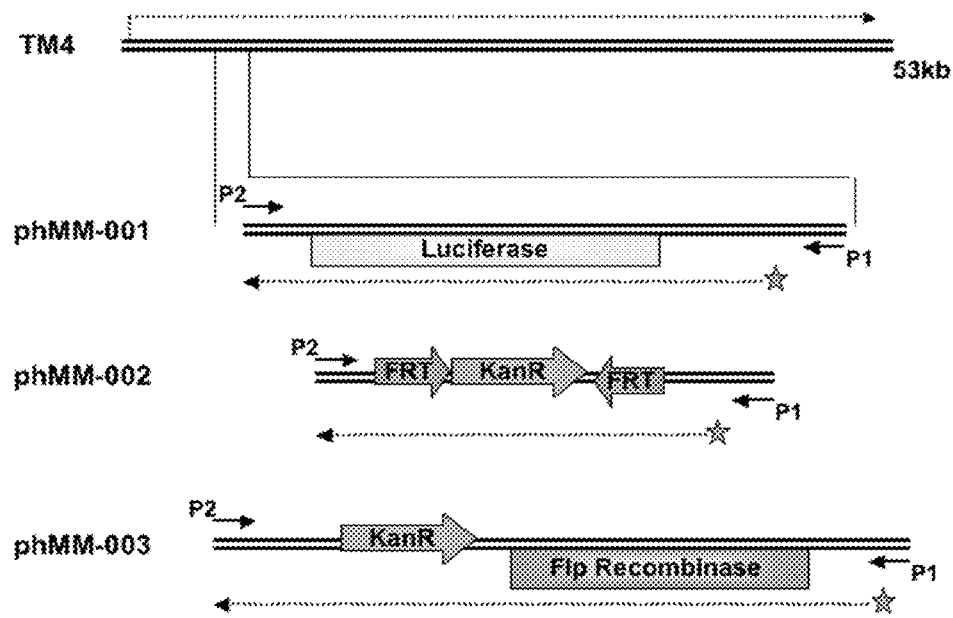
FIG. 11A is a schematic showing the construction of three SML-phage constructs used to test and develop an exemplary Flp recombinase-based SML generation module. phMM-001 contains a standard luciferase reporter gene. In phMM-002 the luciferase gene has been replace with two Frt sites (Flp recognition sites) and a kanamyacin resistance gene. In phMM-003 the lucerifase gene is replaced with sequences encoding a kanamyacin resistance gene and Flp recombinase.
FIG. 11B is a stained agarose gel readout verifying proper integration of the appropriate PCR products in phMM-002 and phMM-03.
Figure 11:
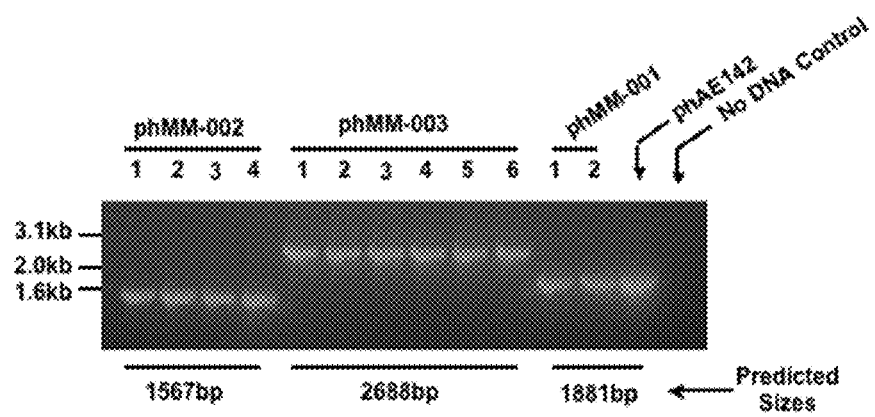

Generation of Flp Recombinase Encoding Mycobacteriophage and FRT Encoding Mycobacteriophage For initial proof of principle experiments, the SML is separated from the recombinase in order to absolutely preclude spurious generation of the SML during growth of phage stocks. Flp mediate inversion of the kanamycin resistance (KanR) cassette (i.e., generation of the SML) is then measured during co-infection of mycobacterial cells with phMM-002 and phMM-003. (FIG. 11A) Three new phasmids were created. A phasmid is a circular DNA molecule that can replicate in *E. Coli* and is maintained via antibiotic selection (not shown). phMM-001 was derived directly from phAE142 bacteriophage DNA by intramolecular ligation with T4 DNA ligase followed by transformation into *E. Coli* DH10B cells. phMM-002 and phMM-003 were created by electroporating linear PCR products into *E. Coli* cells harboring phMM-001 and a separate plasmid expressing the red recombination system from enterobacteria phage 1 which directs homologous recombination of the PCR product into the phMM-001 DNA. The 5' and 3' ends of the PCR products contained 42 nucleotides of DNA homologous to the DNA sequences immediately 5' and 3' of the luciferase gene in order to direct homologous recombination to replace the luciferase open reading frame with the linear PCR product. The PCR products also encoded the KanR cassette to allow for selection of recombinants on kanamycin containing agar. For phMM-002, the linear PCR product encoded the KanR cassette flanked by inverted FRT repeats. The FRT sequence is the consensus DNA binding and recombination site for the Flp recombinase. Inverted FRT repeats mediate inversion of the intervening DNA sequence in the presence of active Flp recombinase. Inversion of this sequence by Flp recombinase constitutes generation of the SML. For phMM-003, the linear PCR product encoded the Flp recombinase adjacent to the KanR cassette for selection of recombinants. In phMM-003, the Flp recombinase open reading frame is under direct transcriptional control of the robust $P_{left}$ promoter (grey star) from mycobacteriophage L5. This promoter also transcribes through the FRT flanked KanR cassette locus, although the KanR open reading frame is encoded on the opposite strand and the KanR polypeptide is not synthesized by translation of $P_{left}$ transcribed RNA. Transcription on the lower strand by $P_{left}$ in phMM-002 allows both RNA as well as DNA-based NAA methods to be used to detect the Flp mediated KanR inversion (i.e. SML generation). P1 and P2 indicate the location and direction of priming of the PCR primer pair used to verify proper, site-specific recombination of the respective PCR products into phMM-001 to create phasmids phMM-002 and phMM-003.

Primers P1 and P2 were used to verify the proper integration of the appropriate PCR products encoding the appropriate functions for phMM-002 and phMM-003. See FIG. 11B. For phMM-001, phMM-002, and phMM-003, individual colonies of *E. Coli* exhibiting the correct antibiotic resistance profile were added to a PCR tube containing the appropriate buffers, Taq enzyme, and primers P1 and P2. Purified DNA from phAE142 was used as a control. PCR was performed for 25 cycles and 10% of the reaction volume was loaded onto a 1% Agaraose/TAE gel impregnated with 1microgram/ml ethidium bromide. DNA size markers were also loaded onto the gel which was run at 80 volts for 45 minutes followed by visualization in ultraviolet light. All isolates for each phasmid produced PCR products exhibiting the same migration through the agarose gel and were of the expected size.

EXAMPLE 7

Mycobacteriophage Bxb1 Integrase Reporter Phage

Integrase-based SML-phage exploit the ability of integrase to mediate recombination between attP and attB sites. As illustrated in FIG. 12, SML-phage are created by inserting the Int, along with attP and attB sites, into the TM4 mycobacteriophage genome under transcriptional control of the $P_{left}$ promoter. Primers P1 and P2 bind to signature tag sequences (T1 and T2) placed on either side of Int, adjacent to the attP and attB sites. P1 and P2 are oriented in opposite directions and are unable to generate a PCR product. Expression of Int from the $P_{left}$ promoter in viable metabolically active *Mycobacteria* leads to recombination between attP and attB sites This reaction generates two products: (1) a new site, attR, in the phage; and (2) a small circular DNA molecule containing the Int gene, T1, T2, and a new site attL. This molecule constitutes generation of the SML, as P1 and P2 are now opposed and can generate a PCR product. Furthermore, because the SML product is circular, it is highly stable and resistant to degradation.

Bacteriophage are extremely easy to grow with high yield. However, during the manufacturing of SML-phage, it is very important to ensure that SML is not generated, so that false positive results due to SML contamination do not occur. The Int SML-phage is designed to ensure that the SML is not expressed during manufacturing.

Expression of the phage-encoded Int is regulated by the $P_{left}$ promoter. This promoter is highly active in *Mycobacteria*, but is exquisitely silenced by the transcriptional repressor gp71 from mycobacteriophage L5 (11). As a second level of control, Xis is employed to prevent any Int enzyme from generating the SML. Thus, any Int synthesized in the presence of gp71 will be inhibited by Xis thereby severely reducing SML generation.

EXAMPLE 8

Feasibility and Validation of a Novel Mycobacteriophage Transciption System to Identify Anti-Microbial Resistant *Mycobacteria*

In one exemplary embodiment a SML-phage is constructed that uses the Sp6 RNA polymerase to generate an otherwise absent phage-encoded RNA (FIG. 13). This is accomplished by inserting into the TM4 mycobacteriophage genome the Sp6 RNA polymerase open reading frame under control of the robust mycobacteriophage L5 $P_{left}$ promoter. Additionally, the Sp6 polymerase promoter consensus sequence is inserted into the phage genome in an otherwise transcriptionally silent locus. During infection of viable *Mycobacteria*, the Sp6 RNA polymerase is expressed from the $P_{left}$ promoter, and can initiate transcription of a reporter sequence downstream of the Sp6 promoter. Sp6-dependent RNA transcripts constitute generation of the SML and can be detected using Reverse Transcription-PCR (RT-PCR) or isothermal RNA-based amplification technologies such as NASBA or TMA.

SML Detection Requires SML-Phage Infection

To demonstrate that the Sp6 RNA polymerase SML-phage can detect viable Mtb, $3 \times 10^7$ H37Rv cells were serially diluted in 7H9 media supplemented with ADC but lacking Tween-80 (Tween-80 interferes with phage infection) and infected with $3 \times 10^7$ plaque forming units (pfu) of the Sp6 SML-phage at 37° C. At the time of infection, RNase A (Sigma Aldrich) was added to the samples to degrade contaminating SML generated during growth of the phage stocks. RNase A was added to a final concentration of 50 pg per $3 \times 10^7$ pfu of SML-phage. At 2 hr post-infection, recombinant murine RNase Inhibitor (New England Biolabs) was added to a final concentration of 1 U/µl in order to inhibit RNaseA activity, precluding RNase A-mediated degradation of SML generated after phage mediated lysis of Mtb. At 4 hr post-infection, insoluble material was removed by centrifugation. Total RNA released into the supernatant by viral mediated lysis was then purified using Qiagen RNAeasy silica columns. Eluted RNA was then treated with DNaseI and the 150 bp SML reporter RNA amplified using RT-PCR.

Figure 14:
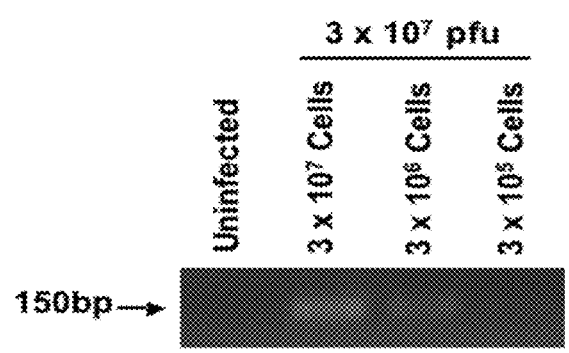
FIG. 14 is a stained agarose gel readout showing the detection of *Mycobacterium* using an exemplary Sp6 RNA polymerase-based SML generation module.

Amplification products were separated by 2% agarose gel electrophoresis and visualized by ethidium bromide staining FIG. 14 demonstrates that SML generation is specific to phage infected cells and the current Sp6 SML-phage prototype can detect at least $3\times10^5$ Mtb cells at a multiplicity of infection (MOI) equal to 100. All amplification products required reverse transcription since omission of reverse transcriptase yielded no detectable amplification products (data not shown). Therefore, the amplification signal observed in SML-phage infected cells is derived from SML RNA synthesis rather than replication of phage genomic DNA.

SML Detection can Differentiate Between Untreated and Drug-Treated Mtb.

Figure 15:
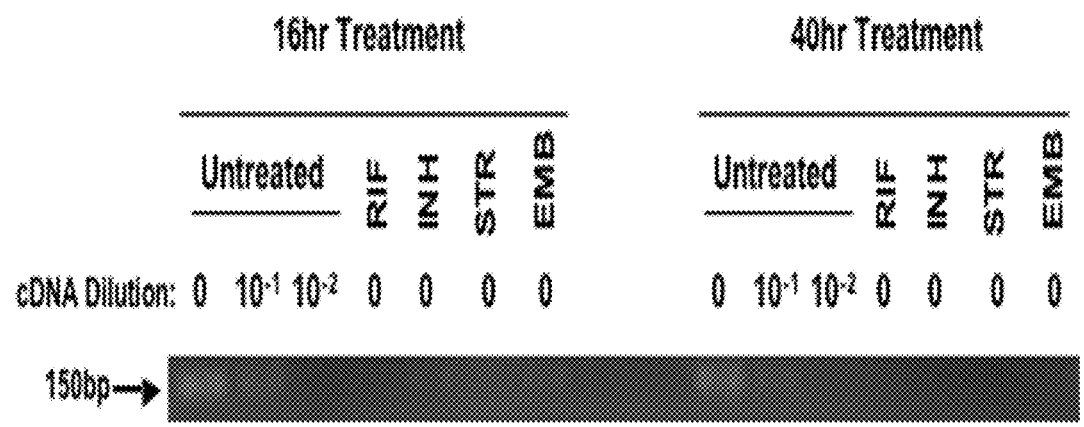
FIG. 15 is a stained agarose readout demonstrating the drug susceptibility testing functionality of the present invention.

The ability of the Sp6 SML-phage to determine the susceptibility of Mtb to first line anti-Tb drugs is demonstrated in FIG. 15. H37Rv cells were treated for either 16 hr or 40 hr with 2 µg/ml RIF, 0.2 µg/ml INH, 2 µg/ml Streptomycin (STR), or 7.5 µg/ml Ethambutol (EMB) at 37° C. The cells were then infected with the Sp6 SML-phage at a MOI of 1 for 4 hr. RNA was then purified and amplified using RT-PCR. $10^{-1}$ and $10^{-2}$ dilutions of the untreated control cDNA were made and amplified to provide an estimation of the signal to noise ratio between untreated and drug treated Mtb. At both 16 and 40 hr of drug exposure, there is a clear difference in SML generation between the untreated and drug treated samples. Cells treated with RIF and STR and infected with the SML-phage generate no detectable SML after either 16 or 40 hr of treatment. This is not surprising because RIF and STR interfere directly and immediately with phage gene expression. For cells treated with INH and EMB and infected with the SML-phage, there is some detectable SML synthesis after 16 hr of drug treatment, which is completely abolished after 40 hr. The level of SML generation in the 16 hr samples is at least 10 fold reduced compared to the untreated control: the amplification product derived from INH and EMB treated cells is less intense than the $10^{-1}$ dilution of cDNA from the untreated control.

INH and EMB do not inhibit SML generation with the same time course as RIF or STR. Whereas RIF directly inhibits existing mycobacterial RNA polymerase enzymes and STR inhibits existing mycobacterial ribosomes, INH and EMB inhibit the synthesis of cell wall components and require turnover of these structures before their effects on phage infection occur. Although after 16 hr of drug exposure the signal to noise ratio is lower in cells treated with INH or EMB compared to RIF or STR, the SML-phage assay clearly demonstrates Mtb drug susceptibility to INH and EMB at this time and improves with incubation up to 40 hr.

Figure 16:
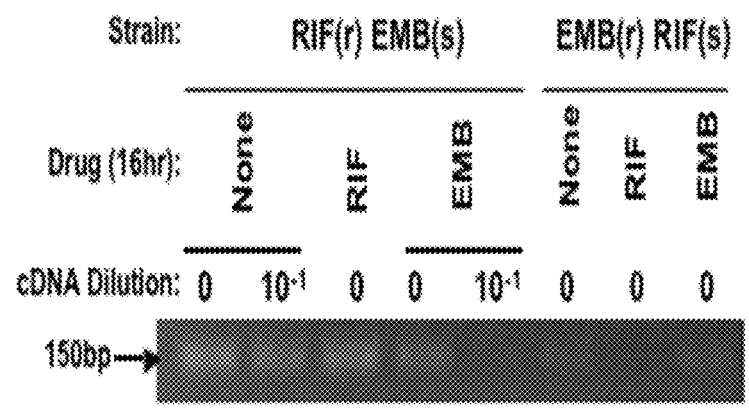
FIG. 16 is a stained agarose readout demonstrating the drug resistance testing functionality of the present invention using multiple drugs.

SML generation can detect Mtb drug resistance to RIF or EMB. The ability of the Sp6 SML-phage to detect drug resistant Mtb strains is demonstrated in FIG. 16. Two singly drug resistant Mtb strains, one resistant to RIF and the other to EMB, were either untreated or treated with RIF and EMB for 16 hr. They were then infected at a MOI=1. At 4 hr post-infection, RNA was purified and amplified using RT-PCR. $10^{-1}$ dilutions of the cDNA derived from both the untreated and EMB-treated RIF-resistant strain were made and amplified to provide an estimation of the signal to noise ratio between both samples. In the case of the RIF-resistant strain, treatment with EMB results in an approximately 10 fold reduction in SML generation compared to the untreated control, whereas there is no observable reduction in SML generation after treatment with RIF. In the case of the EMB resistant strain, treatment with RIF results in no detectable SML, which reflects the potency of RIF in this assay, while SML generation is not decreased after EMB treatment. These data demonstrate that RIF and EMB resistance can be easily detected by SML-phage after as little as 16 hr of drug treatment.

Figure 17:
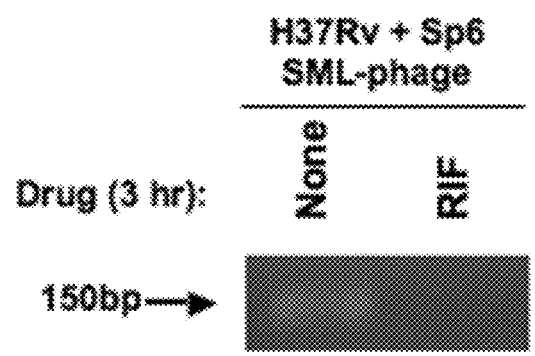
FIG. 17 is a stained agarose gel readout showing the ability to detect drug susceptibility using the SML technology of the present invention within four hours.

Because RIF directly inhibits the host cell RNA polymerase that is essential for phage gene transcription and synthesis of the phage-encoded Sp6 RNA polymerase, a test was conducted to determine whether a 3 hr pretreatment of MTB with RIF is sufficient to preclude SML-generation. H37Rv cells were either left untreated or treated with 2 µg/ml RIF for 3 hr. SML-phage (MOI=1) were then added. At 4 hr post-infection, RNA was purified and amplified using RT-PCR. As shown in FIG. 17, SML generation is dramatically inhibited during infection of cells pre-treated with RIF for only 3 hours. This result suggests the feasibility of the development of a rapid test for RIF resistance for Mtb present in sputum samples within 10 hours.

Mucolytic Agents do not Affect Phage Infection or SML Generation

Figure 18:
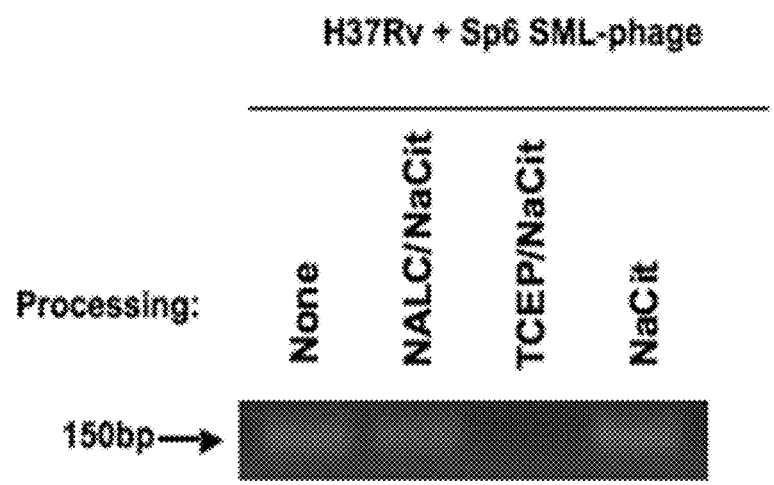
FIG. 18 is a stained agarose gel readout demonstrating that NALC does not interfere with SML-phage infection.

In the effort to create a rapid RIF test using SML-phage technology it was examined whether agents known to efficiently liquefy the mucin matrix present in sputum samples interfered with phage infection and SML-generation. N-acetyl-L-cysteine (NALC) is the most commonly used mucolytic agent. It functions by reducing the intermolecular disulfide bonds that stabilize mucin protein complexes. Tris-Carboxyethylphosphine (TCEP), is another agent that reduces disulfide bonds, but is not commonly used in sputum processing. To evaluate whether NALC and TCEP interfere with phage infection and SML generation, H37Rv cells were diluted by addition of equal volumes of either 7H9-ADC media or 0.5% NALC/2.9% NaCitrate or 200 mM TCEP/2.9% NaCitrate or 2.9% NaCitrate and incubated for one hour at 37° C. The samples were then diluted by addition of 2.5 volumes of 7H9-ADC media and infected with SML-phage at a M01=1 for 4 hr at 37° C. SML RNA was purified and amplified using RT-PCR and products visualized. As shown in FIG. 18, NALC has no effect on phage infection and SML generation, whereas TCEP completely abolishes SML generation.

An alternative mucolytic agent is hypertonic saline (HiSalt). HiSalt breaks down mucus in the lungs of Cystic Fibrosis patients to facilitate expectoration of the mucin plugs blocking bronchioalveolar passages. Additionally, HiSalt liquefies the mucin matrix present in sputum samples derived from TB patients and facilitates diagnosis via smear microscopy at rates similar to NALC (12, 13). We evaluate whether HiSalt was evaluated to determine if it interferes with phage infection, SML generation, and RIF susceptibility. The test indicate that HiSalt has no effect on phage infection and SML generation. Additionally, it does not interfere with the ability of RIF to block SML generation in susceptible cells infected with SML-phage.

Since neither NALC or HiSalt interfere with phage infection and SML generation a SML-based rapid RIF AST may not require decontamination or concentration of Mtb by centrifugation, a capability often absent in peripheral lab facilities in the developing world. Finally, it may also be possible to employ the mucolytic and decontamination agent cetylpyridinium chloride.

EXAMPLE 9

Modified SML-Generation Modules for Solid Affinity Matrix Isolation of SMLs

FIG. 19 illustrates the genetic design of Sp6 Polymerase-based SML-phage that encode various functions to facilitate simplified purification, amplification, and detection of multiple SML RNAs. All SML RNAs will have several functional sequences in common. They are: (1) unique sequences (US), which can be varied so that individual phage express different RNA (US-1, US-2, US-3, etc.), so that a nucleic acid lateral flow detection device can distinguish SML by using distinct capture oligonucleotides that hybridize to the US region of SML RNA; (2) a hairpin (HP) structure at the 3' end of SML RNA to inhibit 3'-5' exonuclease degradation of SML RNA; (3) an aptamer (Apt) sequence known to tightly bind streptavidin that will facilitate rapid and efficient purification of SML RNA after lysis of infected Mtb using streptavidin coated paramagnetic beads; (4) signature tagged sites (T1 & T2) to which amplification primers (P 1 & P2) bind. T1 and T2 are common to all SML-phage so that only one primer pair is used in an amplification reaction; and (5) a universal detection sequence (UD) to which reporter oligonucleotides coupled to either colloidal gold or latex beads will hybridize during nucleic acid lateral flow detection of amplified SMLs.

EXAMPLE 10

Use of RNA Cyclase Ribozyme to Generate Circular SML RNA

SML-generation modules that rely on RNA polymerase to generate the SML result in RNA signals that are the same sequence as their cognate source nucleic acid sequence DNA. Detecting the SML using RT-PCR and similar technologies could yield false positives due to amplification of DNA source nucleic acid sequences in the SML generation module. One way to preclude such false positives is to degrade the SML genaration module using DNase I prior to initiation of the amplification reaction. A system that directs synthesis of a SML RNA whose sequence is distinct from the cognate DNA source nucleic acid sequence in the SML generation module would not require removal of DNA prior to amplification and would permit the use of all nucleic acid amplification technologies capable of using RNA as a substrate.

Figure 22:
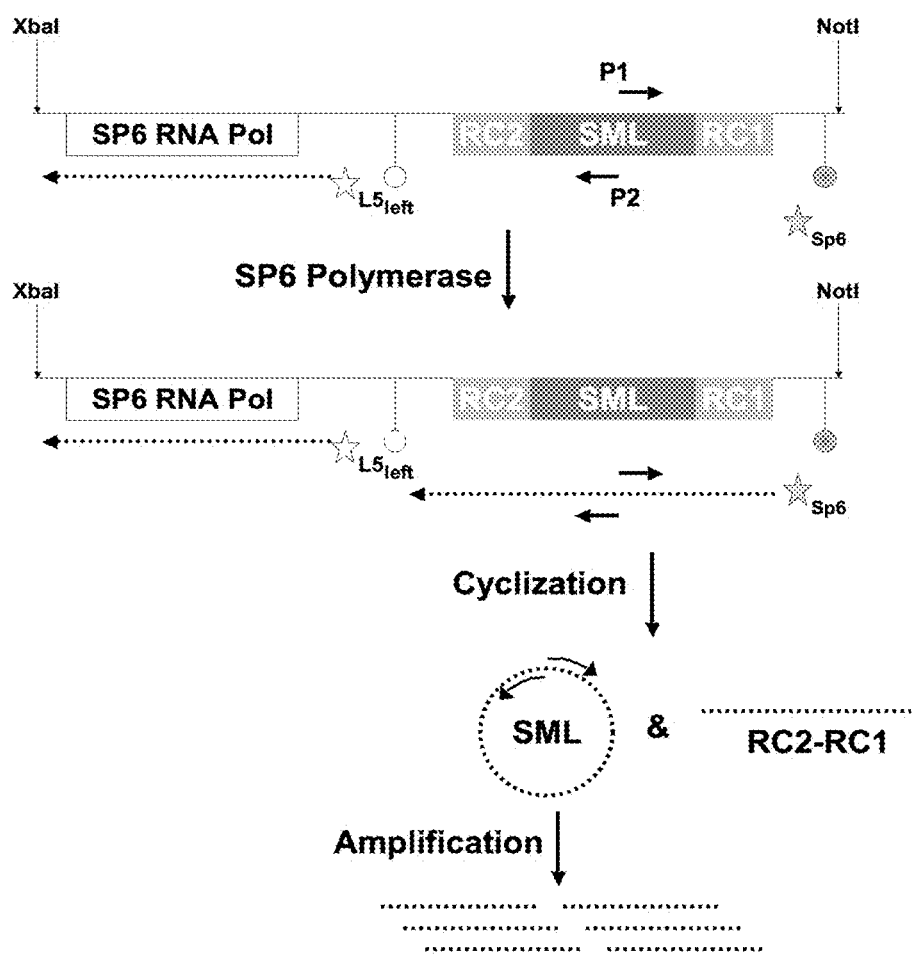
FIG. 22 is a schematic showing an exemplary genetic structure of a Sp6 RNA polymerase/RC cyclase ribozmye-based SML generation module.

As shown in FIG. 22, a SML generation module was designed on an XbaI-NotI fragment and is composed of two sections. The first is the SP6 RNA Polymerase open reading frame (ORF) under transcriptional control of the Mycobacteriophage L5 $P_{left}$ promoter (open star), which directs expression of SP6 Polymerase in *Mycobacteria*. The second section encodes the SP6 consensus promoter (grey star) fused to a downstream DNA sequence, which encodes the SML. SP6 Polymerase-dependent transcription constitutes generation of the SML. Currently, a prototype SML-generation module is incorporated into mycobacteriophage TM4 to create a recombinant reporter mycobacteriophage that delivers the SML-generation cassette to *Mycobacteria*. A DNA sequence downstream of the SP6 promoter will be introduced that encodes the SML flanked by two halves of a sequence that encodes the RNA Cyclase (RC) ribozyme. After transcription of this locus by SP6 Polymerase expressed from $P_{left}$, RNA is synthesized that has one half of RC (RC1) fused to the 5' end of the SML and the other half of RC (RC2) fused to the 3' end of the SML. Once synthesized, the RC elements in the SML RNA mediate circularization of the SML RNA. In addition, the RC RNA sequences fuse to each other as a byproduct. Circularization of the SML constitutes generation of a new RNA sequence that is distinct from the cognate DNA locus in the SML-generation module. This new RNA sequence can be amplified using any type of nucleic acid amplification reaction capable of amplifying a RNA substrate using primers P1 and P2. Although P1 and P2 can bind to the cognate DNA locus in the SML generation module, they are oriented opposite to each other such that they cannot create an amplification product. Circularization of the SML RNA results in Primers P1 and P2 being oriented towards each other on the circular SML RNA substrate and can now mediate amplification of the intervening RNA sequence. This strategy facilitates the use of all amplification technologies capable of using RNA as a substrate to detect SML generation and rules out false positives from the cognate DNA locus in the SML generation module.

To demonstrate that the SML design depicted in FIG. 22 is capable of producing circular RNA, a DNA fragment consisting of the following sequence was synthesized de novo and inserted between the EcoRI and HindIII sites of pUC57 with the 5' end of the sequence fused to the EcoRI site to produce pUC57-Cyclase (FIG. 23A):

(SEQ ID NO: 1)
5'GCGGCCGCaagcagcataaccttttccgtgatggtaacttcacgg taaccaagatgtcgagttaaccacccaaggccatccgtcaggatggcc ttgtttaaacctctGCACAGGCACGTCTGGATGCACGTCGCCGCGCAG

GTATGGCTCGCGGTCTTTAATTGCCTATTTAGGTGACACTATAGAAGT

TAATTAATTGGTTCTACATAAATGCCTAACGACTATCCCTTTGGGGAG

TAGGGTCAAGTGACTCGAAACGATAGACAACTTGCTTTAACAAGTTGG

AGATATAGTCTGCTCTGCATGGTGACATGCAGCTGGATATAATTCCGG

GGTAAGATTAACGACCTTATCTGAACATAATGCTACCGTTTAATATTC

GTGGCCTTTGTCACCGACGCCTACTCGAGGGGTTAATGTAAAAACCGA

CCAGAATCATGCAAGTGCGTAAGATAGTCGCGGGCCGGGAAAAACATT

GGCCCCTCGAGGGACAACGCCGAATTGCGAAGGGCTATCAGTTTAATG

TGCGTAAACGACCACATCAACCATGCATGATCTTCTACTACATCAGCT

TTTAGATTTTTCACGCTTACTGCTTTTTTCTTCCCAAGATCGAAAATT

TACTGAATTAACAATGGATTCTGAGGTTGCTGCTTTGGTTATTGATAA

CGGTTCTGGTATGTGTAAAGCCGGAGCTCAGATGTTTTCTTGGGTTAA

TTGAGGCCTGAGTATAAGGTGACTTATACTTGTAATCTATCTAAACGG

GGAACCTCTCTAGTAGACAATCCCGTGCTAAATTGTAGGACTGCCCTC

CGGACCTATGCCCTATCTACCTTGCGTAGGTAGGGTTCTTTTTAGCAT

AACCCCTTGGGGCCTCTAAACGGGTCTTGAGGGGTTTTTTTATCCTTA

ATCCTTAGCGAAAGCTAAGGATTTTTTTT-3'

Figure 23:
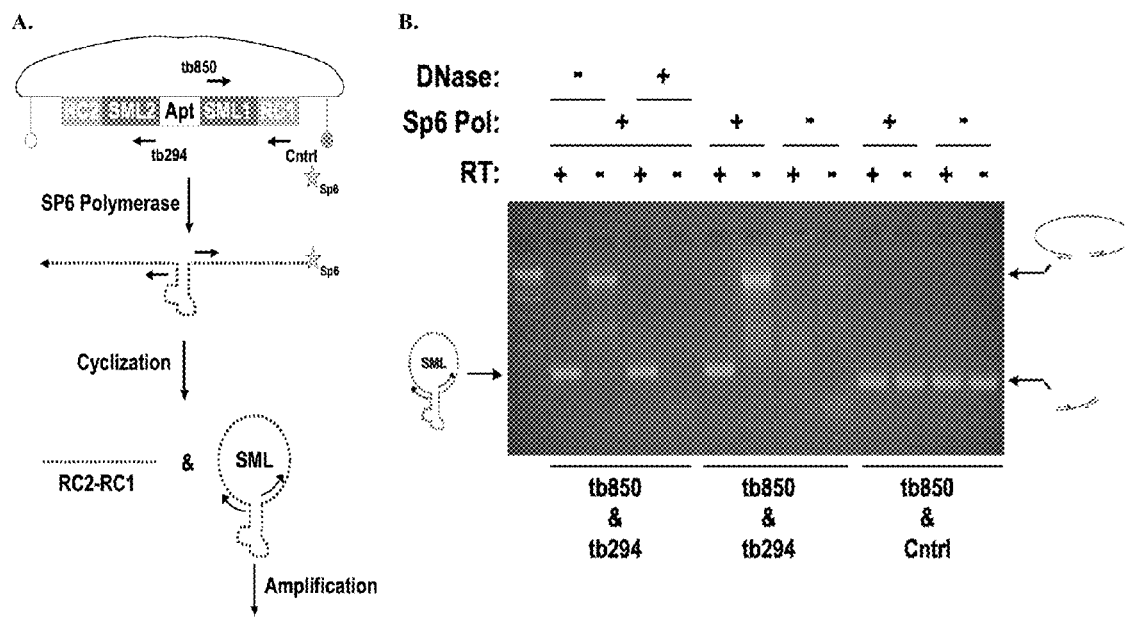
FIG. 23 (A) depicts the plasmid pUC57-Cyclase which contains an exemplary Sp6 RNA polymerase promoter/RC cyclase ribozyme-based SML source nucleic acid, and (B) is a stained agarose gel readout showing detection of a SML generated from in vitro transcription of an exemplary Sp6 RNA polymerase promoter/RC cyclase ribozyme-based SML source nucleic acid depicted in (A).

This fragment contains the section of the SML generation module depicted in FIG. 22 that encodes the SP6 consensus promoter (grey star) fused to a downstream DNA sequence, which encodes the SML and includes the upstream and downstream transcription termination signals. In addition, pUC57-Cyclase includes an aptamer sequence as described in FIG. 26 and Example 11. The sequence that encodes the Circular RNA produced after transcription from the SP6 promoter is underlined and a 265 bp portion detected by RT-PCR using primers tb850 (5'-TAGGCGTCGGTGACAAAGGCCACG-3') (SEQ ID NO: 2) and tb294 (5'-GGACAACGCCGAAT-TGCGAAGGGC-3') (SEQ ID NO: 3) as described by Garcia-Quintanilla et al. for balanced hemi-nested PCR detection of the IS6110 locus in *Mycobacterium tuberculosis* (14). The Cntrl primer in combination with tb850 can utilize the intervening plasmid sequence as well as un-spliced RNA as templates and generates a product of similar size compared to tb850 and tb294. To demonstrate that this fragment encodes the ability to produce circular SML RNA, 50 ng pUC57-Cyclase was in vitro transcribed in a 50 µl reaction volume using purified SP6 RNA Polymerase (New England Biolabs—NEB) supplemented with 4 mM of each NTP, 2 mM $MgCl_2$ and 1 U/µl murine ribonuclease inhibitor (NEB) for 1 hr at 40° C. After in vitro transcription, samples were immediately reverse transcribed and PCR amplified or pUC57-Cyclase was destroyed by the addition of DNaseI. After incubation with DNaseI, EDTA was added to a final concentration of 18 mM and the samples heat inactivated for 10 mins at 75° C. Reverse transcription for all samples was performed in 20 µl volume using 5 µl of undigested or DNaseI treated RNA with AMV RT (NEB) and primer tb850 for 30 mins at 42° C. Following reverse transcription, cDNA was PCR amplified using primers tb850 and tb294 or tb850 and Cntrl. Amplification products were separated via 2% agarose gel electrophoresis and stained with ethidium bromide. FIG. 23B demonstrates that circular RNA is produced after in vitro transcription of pUC57-Cyclase by purified SP6 Polymerase because a 265 bp amplification product using primers tb850 and tb294 requires both RT and SP6 polymerase and is not affected by DNaseI treatment performed after in vitro transcription but before reverse transcription. Primers tb850 and Cntrl produce an amplification product similar in size to that produced by tb850 and tb294, but it does not require the addition of RT or SP6 Polymerase. Therefore, circular SML RNA is produced by the DNA construct outlined in FIG. 23A.

EXAMPLE 11

Incorporation of Aptamers into SML RNA to Facilitate Rapid and Efficient Purification A key step in diagnostics that employ nucleic acid amplification is the purification of target nucleic acids away from amplification inhibitors derived from the clinical specimen. Another concern is amplification of target nucleic acids that constitute a minute minority of total nucleic acid in the sample. This is especially problematic when highly conserved sequences such as ribosmomal RNA are the targets. Ideally, the target nucleic acid is selectively purified away from other nucleic acids, as well as amplification inhibitors. Approaches such as sequence-specific capture using biotinylated oligonucleotides attached to a solid support like streptavidin-coated paramagnetic beads are routinely employed to selectively purify and concentrate target nucleic acids prior to amplification. Although effective, sequence specific capture using oligonucleotides is complex since the target nucleic acids often must first be denatured to melt secondary structure and allow the oligonucleotide to hybridize to its complement present in the target.

Here, a method that permits selective purification of the SML RNA without the need for denaturation or sequence-specific oligonucleotide capture is described. This method may dramatically simplify the purification and concentration of SML RNA, thereby reducing assay complexity and cost. As illustrated in FIG. 24, a streamlined selective SML purification system is designed by inserting a DNA sequence internal to the SML sequence in the SML-generation module, which is also internal to the RNA Cyclase Ribozyme gene. This sequence codes for any number of RNA sequences, known as aptamers (Apt), that have the ability to bind solid matrixes or solid supports (SS) or components attached to SS. A specific example is the streptavidin-binding aptamer described by Srisawat and Engelke (15). Incorporation of the sequence encoding the streptavidin binding aptamer in the position illustrated in FIG. 24 results in the creation of a circular SML RNA that includes the RNA aptamer. This aptamer has been shown to bind streptavidin with high affinity in a native state,[12] which obviates the need for trans-acting factors like biotinylated oligonucleotides to mediate binding to the SS and does not require denaturation either though heating or by the addition of chemical denaturants such as formalin, or addition of guanidinium salts. Thus, SML RNA can be selectively purified using a SS coated with streptavidin by simply adding the matrix to a liquid in which the SML RNA is dissolved or passing that liquid through a column or syringe filter packed with an appropriate SS to which the aptamer binds. In addition, it may be possible to perform amplification of the SML RNA while it is still attached to the SS through the aptamer-strepatvidin complex since the SML should be sufficiently in solution rather than in an interphase between liquid and solid states.

EXAMPLE 12

Use of Group II Introns in the SML Generation Module to Generate a DNA-Based SML To create a SML-generation module that creates a DNA-based SML and is regulated by the addition of a small molecule that specifically inhibits the SML generation enzyme, a mobile Group II intron-based SML generation module was designed. For many Group II introns, reverse transcriptase (RT) activity of an Intron Encoded Protein (IEP) is absolutely essential for mobility of the intron. Since intron mobility constitutes SML generation in this system and requires RT activity, small-molecule reverse transcriptase inhibitors (RTI) active against the RT activity of the IEP can be used to preclude retrohoming during phage manufacturing.

Group II introns are selfish DNA elements capable of inserting into DNA at specific sites (17, 18). Generally, they interrupt protein-coding regions of genomic DNA and are removed post-transcriptionally to regenerate the open reading frame (ORF). Splicing of many Group II introns requires the maturase activity of the IEP. In addition to maturase activity, IEPs often exhibit endonuclease and RT activities. Once synthesized, the IEP binds the intron RNA and stabilizes its secondary structure to accomplish two goals. The first is splicing of the intron RNA to fuse the exon sequences and regenerate a complete ORF in the messenger RNA. The second is insertion of the intron RNA into an "intronless" allele of the ORF in the cell or phage genome. The insertion of the intron sequences into an intronless allele is called retrohoming and results in the re-creation of the same intron-exon junctions of the previous intron-interrupted allele. Once the intron RNA is inserted into the intronless allele, it must be converted into DNA to become a permanent fixture of the cell genome. For many Group II introns, this is accomplished by the RT activity of the IEP. Small-molecule reverse transcriptase inhibitors (RTI) active against the RT activity of the IEP can be used to preclude retrohoming during phage manufacturing or construction of a Group II intron-based SML generation module.

The L1.trB intron from *Lactococcus lactis* is the best characterized and most widely studied Group II intron. L1.1trB is composed of two elements: the intron RNA and LtrA, the IEP. LtrA is a multi-domain protein with RT, endonuclease and maturase activities. LtrA is absolutely essential for retrohoming of the L1.1trB intron. Spread of this selfish DNA element is accomplished first by transcription of the L1.1trB intron, including the LtrA ORF. Once LtrA is translated, it binds the L1.1trB intron and the maturase activity of the enzyme stabilizes the intron RNA secondary structure and promotes splicing of the intron out of the mRNA. Next, elements of the intron RNA bind to homologous DNA elements in the intronless allele. At this point, the endonuclease activity of LtrA makes a double stranded cut in the DNA. Once the cut is made, the intron RNA fuses to the 5' end of an exposed DNA nucleotide to create a DNA-RNA junction. At this stage, the intron RNA has been inserted into the genomic locus and must be converted into DNA in order to become a permanent addition to the genome. This is accomplished by the RT activity of LtrA, which utilizes the other strand of the double strand cut as a primer for reverse transcription of the inserted intron RNA. Once the cDNA is completed, host RNaseH and DNA repair enzymes degrade the intron RNA and complete synthesis of the second DNA strand.

FIG. 25 illustrates how a SML generation module employing the L1.1trB intron would be constructed. In the wildtype L1.1trB intron, the LtrA ORF is internal to the intron. Work by Lambowitz's group demonstrated that if the LtrA ORF is deleted from its position in the L1.1trB intron to create L1.1trBΔORF, and expressed downstream from L1.1trBΔORF by a heterologous promoter, the efficiency of retrohoming approaches 100% (19). A similar arrangement will be replicated in the SML generation module. As depicted in FIG. 25, the intron RNA (L1.1trBΔORF) is transcribed by host RNA polymerase from the constitutive $P_{hsp60}$ promoter and is terminated at a downstream transcription termination site in order to not interfere with expression of LtrA from the $P_{left}$ promoter. When both $P_{hsp60}$ and $P_{left}$ are active, the two elements required for retrohoming, namely, the L1.1trBΔORF RNA and LtrA, accumulate, and a copy of L1.1trBΔORF is inserted into a target site (inverted E2E1) placed upstream of $P_{hsp60}$. Once L1.1trBΔORF is inserted into the target site and reverse transcribed, two binding sites for primer P1 exist. Furthermore, as illustrated in FIG. 25, the E1E2 target site is in reverse orientation compared to E1 and E2 fused to L1.1trBΔORF under $P_{hsp60}$ transcriptional control, and directs the insertion of the L1.1trBΔORF intron into the target site in reverse orientation. This results in the P1 binding sites being oriented towards each other such that P1 can generate an amplification product consisting of the intervening sequence. Without retrohoming of L1.1trBΔORF into the target site, there is only one binding site for primer P1 and thus amplification cannot occur.

Retrohoming will be controlled by inhibiting both expression of LtrA and its RT activity. As illustrated in FIG. 26, expression of LtrA from the $P_{left}$ promoter will be downregulated by expression in trans of the mycobacteriophage L5 gp71 polypeptide from the host cell genome. Gp71 is a potent inhibitor of transcription elongation from $P_{left}$. Cell lines that constitutively express gp71 exist and have been used to down-regulate expression of transgenes incorporated into reporter mycobacteriophage under $P_{left}$ transcriptional control (20). However, transcriptional inhibition by gp71 is not absolute and some LtrA is synthesized (21). To preclude retrohoming by the residual amount of LtrA that accumulates, cells containing the L1.LtrB-based SML generation module will be incubated with a small molecule RTI that exhibits sufficient activity against LtrA. By controlling both LtrA expression and RT activity, it should be possible to exert total control over retrohoming and SML synthesis.

Another advantage of employing L1.1trB or any other similar Group II intron, is that specific bases in L1.1trB and the exon sequences can be altered to direct retrohoming to alternative sites (22). It may be possible to target L1.1trB to a new site such that after retrohoming, the inserted copy of L1.1trB is flanked by recombinase binding sites, which in the presence of the recombinase, remove and circularize the inserted L1.1trB. This would also result in the recreation of the L1.1trB homing site to facilitate a second insertion event. This strategy would allow the SML generation system to make many copies of the SML, and, once created, the SML would not be part of the SML generation module. This would facilitate removal of the SML from the SML-phage preparation to ensure there is no carryover into a test for bacterial viability or drug resistance.

REFERENCES

1. Dye et al., 1. Am. Med. Association, 282, 677-686, (1999); and 2000 WHO/OMS Press Release
2. Merck Manual 1992
3. "Ending Neglect: The Elimination of Tuberculosis in the United States" ed. L. Geiter Committee on the Elimination of Tuberculosis in the United States Division of Health Promotion and Disease Prevention, Institute of Medicine. Unpublished.)
4. Murray et al., *Medical Microbiology*, The C.V. Mosby Company 219-230 (1990).
5. Piddhesh et al. "DNA-based Therapeutics and DNA Delivery Systems: A comprehensive Review." AAPS Journal. 2005; 7(1):E61-E77.
6. Ford et al. Synthesis of circular RNA in bacteria and yeast using RNA cylcase ribozymes derived from a group I intron of phage T4. Proc Natl Acad Sci U.S.A. 1994; 91:3117-21.
7. Piddhesh et al. "DNA-based Therapeutics and DNA Delivery Systems: A comprehensive Review." AAPS Journal. 2005; 7(1):E61-E77.
8. Ghosh P, Pannunzio N R, Hatfull G F, 2005. Synapsis in phage Bxb1 integration: selection mechanism for the correct pair of recombination sites. J Mol Biol 349: 331-48.
9. Ford et al. Synthesis of circular RNA in bacteria and yeast using RNA cylcase ribozymes derived from a group I intron of phage T4. Proc Natl Acad Sci U.S.A. 1994; 91:3117-21.
10. Piddhesh et al. "DNA-based Therapeutics and DNA Delivery Systems: A comprehensive Review." AAPS Journal. 2005; 7(1):E61-E77.
11. Nesbit C E, Levin M E, Donnelly-Wu M K, Hatfull G F, 1995. Transcriptional regulation of repressor synthesis in mycobacteriophage L5. Mol Microbiol 17: 1045-56.
12. Ganoza C A, Ricaldi J N, Chauca J, Rojas G, Munayco C, Agapito J, Palomino J C, Guerra H, 2008. Novel hypertonic saline-sodium hydroxide (HS-SH) method for decontamination and concentration of sputum samples for *Mycobacterium tuberculosis* microscopy and culture. J Med Microbiol 57: 1094-8.
13. Ricaldi J N, Guerra H, 2008. A simple and improved method for diagnosis of tuberculosis using hypertonic saline and sodium hydroxide to concentrate and decontaminate sputum. Trop Doct 38: 97-9.
14. Garcia-Quintanilla A, Garcia L, Tudo G, Navarro M, Gonzalez J, Jimenez de Anta M T. Single-tube balanced heminested PCR for detecting *Mycobacterium tuberculosis* in smear-negative samples. J Clin Microbiol 2000; 38:1166-9.
15. Srisawat C, Engelke D R. Streptavidin aptamers: affinity tags for the study of RNAs and ribonucleoproteins. RNA 2001; 7:632-41.
16. Garcia-Quintanilla A, Garcia L, Tudo G, Navarro M, Gonzalez J, Jimenez de Anta M T. Single-tube balanced 16. heminested PCR for detecting *Mycobacterium tuberculosis* in smear-negative samples. J Clin Microbiol 2000; 38:1166-9.
17. Lambowitz A M, Zimmerly S. Mobile group II introns. Annu Rev Genet 2004;38:1-35.
18. Lambowitz A M, Zimmerly S. Group II Introns: Mobile Ribozymes that Invade DNA. Cold Spring Harb Perspect Biol 2010.
19. Guo H, Karberg M, Long M, Jones J P, 3rd, Sullenger B, Lambowitz A M. Group II introns designed to insert into therapeutically relevant DNA target sites in human cells. Science 2000; 289:452-7.
20. Bardarov S, Jr., Dou H, Eisenach K, et al. Detection and drug-susceptibility testing of *M. tuberculosis* from sputum samples using luciferase reporter phage: comparison with the *Mycobacteria* Growth Indicator Tube (MGIT) system. Diagn Microbiol Infect Dis 2003; 45:53-61.
21. Brown K L, Sarkis G J, Wadsworth C, Hatfull G F. Transcriptional silencing by the mycobacteriophage L5 repressor. EMBO J 1997; 16:5914-21.
22. Karberg M, Guo H, Zhong J, Coon R, Perutka J, Lambowitz A M. Group II introns as controllable gene targeting vectors for genetic manipulation of bacteria. Nat Biotechnol 2001; 19:1162-7.

We claim:

1. A vector encoding a surrogate marker locus (SML) generation module, the SML generation module comprising a nucleic acid sequence encoding a polypeptide or a catalytic nucleic acid and a source nucleic acid sequence from which the polypeptide or catlytic nucleic acid generates a distinct surrogate marker locus de novo, wherein the vector is a bacteriophage.

2. The vector of claim 1, wherein the polypeptide is selected from one or more of the following; a DNA recombinase, a RNA recombinase, a RNA polymerase, a DNA polymerase, a transcription factor, a sigma factor, a DNA methylase, a DNA demethylase, a DNA restriction endonuclease, a DNA ligase, a RNA ligase, a histone acetylase, a histone deacytlase, a uridine deaminase, a reverse transcriptase and a RNA maturase.

3. The vector of claim 1, wherein the catalytic nucleic acid is selected from one or more of the following; a RNA cyclase ribozyme, a group I intron, a group II intron, a riboswitch, a gene regulation ribozyme, and RNase P.

4. The vector of claim 1, wherein the source nucleic acid further encodes an isolation aptamer sequence for incorporation into the SML.

5. A method for creating a surrogate marker locus (SML) in cells comprising
   introducing into a cell a bacteriophage vector encoding a SML generation module, wherein the SML generation module comprises a nucleic acid sequence encoding a nucleic acid or nucleotide modifying function, wherein expression of the nucleic acid or nucleotide modifying function generates de novo, a distinct SML from a source nucleic acid sequence; and
   detecting the SML.

6. The method of claim 5, wherein the SML generation module further comprises a source nucleic acid from which the nucleic acid modifying function generates the SML.

7. The method of claim 5, wherein the nucleic acid or nucleotide modifying function is provided by a polypeptide or a catalytic nucleic acid.

8. The method of claim 7, wherein the polypeptide is selected from one or more of the following; a DNA recombinase, a RNA recombinase, a RNA polymerase, a DNA polymerase, a transcription factor, a sigma factor, a DNA methylase, a DNA demethylase, a DNA restriction endonuclease, a DNA ligase, a RNA ligase, a histone acetylase, a histone deacytlase, a uridine deaminase, a reverse transcriptase and a RNA maturase.

9. The method of claim 7, wherein the catalytic nucleic acid is selected from one or more of the following; a RNA cyclase ribozyme, a group I intron, a group II intron, a riboswitch, a gene regulation ribozyme, and RNase P.

10. A method for determining the viability of microbes comprising:
    introducing a bacteriophage vector encoding a SML generation module to a microbe, wherein the SML generation module comprises a nucleic acid sequence encoding a polypeptide or a catalytic nucleic acid, wherein expression of the polypeptide or catalytic nucleic acid generates, de novo, a distinct SML from a source nucleic acid sequence; and
    detecting generation of the SML, wherein detection of the surrogate marker locus indicates that the infectious agent is viable.

11. The method of claim 10, wherein the bacteriophage is specific for *Mycobacterium*.

12. The method of claim 10, wherein the polypeptide is selected from one or more of the following; a DNA recombinase, a RNA recombinase, a RNA polymerase, a DNA polymerase, a transcription factor, a sigma factor, a DNA methylase, a DNA demethylase, a DNA restriction endonuclease, a DNA ligase, a RNA ligase, a histone acetylase, a histone deacytlase, a uridine deaminase, a reverse transcriptase and a RNA maturase.

13. The method of claim 10, wherein the catalytic nucleic acid is selected from one or more of the following; a RNA cyclase ribozyme, a group I intron, a group II intron, a riboswitch, a gene regulation ribozyme, and RNase P.

14. The method of claim 10, wherein the source nucleic acid sequence further encodes an isolation aptamer.

15. The method of claim 10, further comprising determining the metabolic state of the microbe by determining a microbe genomic marker level using a nucleic acid detection method and comparing the microbe genomic marker level to the SML level, wherein detection of lower microbe genomic levels compared to SML levels indicates the microbe is metabolically active and wherein detection of higher microbe genomic levels compared to SML levels indicates the microbe is dormant.

16. A method for determining drug suceptiblity of a microbes comprising:
    exposing a test sample to a drug composition;
    incubating the test sample with a bacteriophage encoding a SML generation module, wherein the SML generation module comprises a nucleic acid sequence encoding a catalytic nucleic acid, wherein expression of the catalytic nucleic acid generates a SML, and
    detecting the presence of the SML, wherein detection of the SML indicates the test sample contains a microbe that is resistant to the drug composition.

17. The method of claim 16, wherein the microbe is a *Mycobacterium*.

18. The method of claim 16, wherien the sample is a body fluid sample, an industrial sample, or an environmental sample.

19. The method of claim 16, wherein incubating the test sample comprises incubating the test sample with multiple SML generation modules.

20. A vector encoding a surrogate marker locus (SML) generation module, the SML generation module comprising a nucleic acid sequence encoding a recombinase and a source nucleic acid, the source nucleic acid comprising a first recombinase recognition site, a second recombinase recognition site, and one or more signature tag sequences between the first recombinase recognition sequence and the second recombinase recognition sequence, wherein the first and second recobinase recognition sites are specific to the recombinase.

21. A vector encoding a surrogate marker locus (SML) generation module, the SML generation module comprising a nucleic acid sequence encoding a RNA polymerase and a source nucleic acid, the source nucleic acid comprising a sequence encoding a first portion of a RNA cyclase ribozyme, a sequence encoding a second portion of a RNA cyclase ribozyme, and two signature tag sequences located between the sequence encoding a first portion of a RNA cyclase ribozyme and the sequence encoding a second portion of a RNA cylcase ribozyme, and wherein the source nucleic acid is under the transcriptional control of a promoter specific to the RNA polymerase.

22. A vector encoding a surrogate marker locus (SML) generation module, the SML generation module comprising a sequence encoding a Intron Encoded Protein (IEP) under the control of a first promoter, a group II intron sequence lacking an internal IEP under the control of a second promoter, a first and second exon sequence, a first copy of the first and second exon sequences flanking either side of the group II intron sequence, and an inverted second copy of the first and second exon sequences located adjacent to each other and upstream of the second promoter.

23. The vector of claim 20, wherein the source nucleic acid further encodes an isolation apatamer sequence for incorporation into the SML.

24. The vector of claim 21, wherein the source nucleic acid further encodes an isolation apatamer sequence for incorporation into the SML.

25. The vector of claim 22, wherein the SML generation module further comprises an isolation aptamer sequence for incorporation into the SML.

26. A method for creating a surrogate marker locus (SML) in a cell comprising: introducing into the cell the vector of claim 20, 21, or 22, wherein expression of the nucleic acid sequence encoded by the SML generation module of the vector generates de novo, a distinct SML; and detecting the SML.

27. The method of claim 26, wherein the vector is a bacteriophage.

28. The method of claim 27, wherein the bacteriophage is specific for *Mycobacterium*.

29. The method of claim 26, wherein the vector further encodes an isolation aptamer for incorporation into the SML.

30. A method for determining the viability of microbes comprising:
introducing into a microbe the vector of claim 20, 21, or 22, wherein expression of the nucleic acid sequence encoded by the SML generation module of the vector generates de novo, a distinct SML; and
detecting generation of the SML, wherein detection of the surrogate marker locus indicates that the infectious agent is viable.

31. The method of claim 30, wherein the vector is a bacteriophage.

32. The method of claim 31, wherein the bacteriophage is specific for *Mycobacterium*.

33. The method of claim 30, wherein the vector further encodes an isolation aptamer for incorporation into the SML.

34. The method of claim 30, further comprising:
determining the metabolic state of the microbe by determining a microbe genomic marker level using a nucleic acid detection method;
and comparing the microbe genomic marker level to the SML level, wherein detection of lower microbe genomic levels compared to SML levels indicates the microbe is metabolically active and wherein detection of higher microbe genomic levels compared to SML levels indicate the microbe is dormant.

35. A method for determining the drug susceptibility of a microbes drugs comprising:
exposing a test sample to a drug composition;
incubating the test sample with the vector of claim 21, 22, or 23, wherein expression of the nucleic acid sequence encoded by the SML generation module of the vector generates de novo, a distinct SML; and
detecting the presence of the SML, wherein detection of the SML indicates the test sample contains a microbe, that is resistant to the drug compositions.

36. The method of claim 35, wherein the vector is a bacteriophage.

37. The method of claim 36, wherein the bacteriophage is specific for *Mycobacterium*.

38. The method of claim 35, wherein the microbe is a *Mycobacterium*.

39. The method of claim 35, wherein the test sample is a body fluid sample, an industrial sample, or an environmental sample.

40. The method of claim 35, where the incubating step comprising incubating the test sample with multiple SML generation modules.

* * * * *